(12) United States Patent
Ronsin et al.

(10) Patent No.: US 6,875,844 B1
(45) Date of Patent: Apr. 5, 2005

(54) PEPTIDE COMPOUNDS DERIVED FROM A SHIFTED ORF OF THE ICE GENE

(75) Inventors: Christophe Ronsin, Clamart (FR); Véronique Scott, Champigny (FR); Frédéric Triebel, Versailles (FR)

(73) Assignee: Institut Gustave Roussy, Villejuif (FR)

( * ) Notice: Subject to any disclaimer, the term of this patent is extended or adjusted under 35 U.S.C. 154(b) by 0 days.

(21) Appl. No.: 10/019,219

(22) PCT Filed: Jun. 27, 2000

(86) PCT No.: PCT/FR00/01791

§ 371 (c)(1),
(2), (4) Date: Dec. 28, 2001

(87) PCT Pub. No.: WO01/00784

PCT Pub. Date: Jan. 4, 2001

(30) Foreign Application Priority Data

Jun. 28, 1999 (FR) .............................. 99 08224

(51) Int. Cl.⁷ ..................... C07K 1/100; A61K 38/00; A01N 37/18
(52) U.S. Cl. .................... 530/350; 530/300; 514/2
(58) Field of Search ................ 530/350, 300; 514/2; 435/7.1, 7.8, 7.92

(56) References Cited

FOREIGN PATENT DOCUMENTS

| WO | WO 9729183 | 8/1997 |
| WO | WO 9855133 | 12/1998 |
| WO | WO 9918206 | 4/1999 |

OTHER PUBLICATIONS

Kato et al. (PIR Database, Accession No. JQ0137, 1996).*
Burgess et al., J of Cell Bio. 111:2129–2138, 1990.*
Lazar et al. Molecular and Cellular Biology 8:1247–1252, 1988.*
Bellone et al. Immunology Today, v20 (10), 1999, pp. 457–462.*
Anderton, S., Immunology, vol. 104, pp. 367–376, 2001.*
Schwer et al. "H. sapiens mRNA for putative carboxylesterase," Online!, Apr. 28, 1997.
Schwer et al. "Molecular cloning and characterization of a novel putative carboxylesterase, present in human intestine and liver," *Biochemical and Biophysical Research Communications* (1997), vol. 233, No. 1, pp. 117–120.
Pindel et al. "Human carboxylesterase (hCE–2) mRNA, complete cds.," Online!, Jul. 10, 1996.
Pindel et al., "Purification and cloning of a broad substrate specificity human liver carboxylestarase that catalyzes the hydrolysis of cocaine and heroin," *Journal of Biological Chemistry* (1997), vol. 272, No. 23, pp. 14769–14775.
Sone, T. et al. "Homo sapiens mRNA for carboxylesterease, complete cds.," Online!, Nov. 25, 1997.
Herr, Wolfgang et al. "The use of computer–assisted video image analysis for the quantification of CD8+ T lymphocytes producing tumor necrosis factor alpha spots in response to peptide antigens.," *Journal of Immunological Methods 1997* (1997), vol. 203, No. 2, pp. 141–152.
Malarkannan, Subramaniam et al. "A rare cryptic translation product is presented by K–b major histocompatiblity complex class I molecule to alloreactive T cells.," *Journal of Experimental Medicine 1995* (1995), vol. 182, No. 6, pp. 1739–1750.
Shastri, Nilabh et al. "Major histocompatibility class I molecules can present cryptic translation Products to T–Cells.," *Journal of Biological Chemistry 1995* (1995), vol. 270, No. 3, pp. 1088–1091.
Ronsin, C. et al. "A non–AUG–defined alternative open reading frame of the intestinal carboxyl esterase mRNA generates an epitope recognized by renal cell carcinoma–reactive tumor–infiltrating lymphocytes in situ." *Journal of Immunology* (1999), vol. 163, No. 1, pp. 483–490.

* cited by examiner

Primary Examiner—Gary B. Nickol
(74) Attorney, Agent, or Firm—Foley & Lardner LLP

(57) ABSTRACT

The present invention relates to a peptide compound which causes a tumor-specific T response, and which comprises a sequence of at least 8 consecutive amino acids of the peptide sequence encoded by a frame-shifted sequence of the iCE gene. The invention also relates to a pharmaceutical composition comprising said peptide compound and to the use of these compounds for manufacturing a medicinal product intended for treating cancer, in particular for treating solid tumors.

7 Claims, 10 Drawing Sheets

Figure 4:
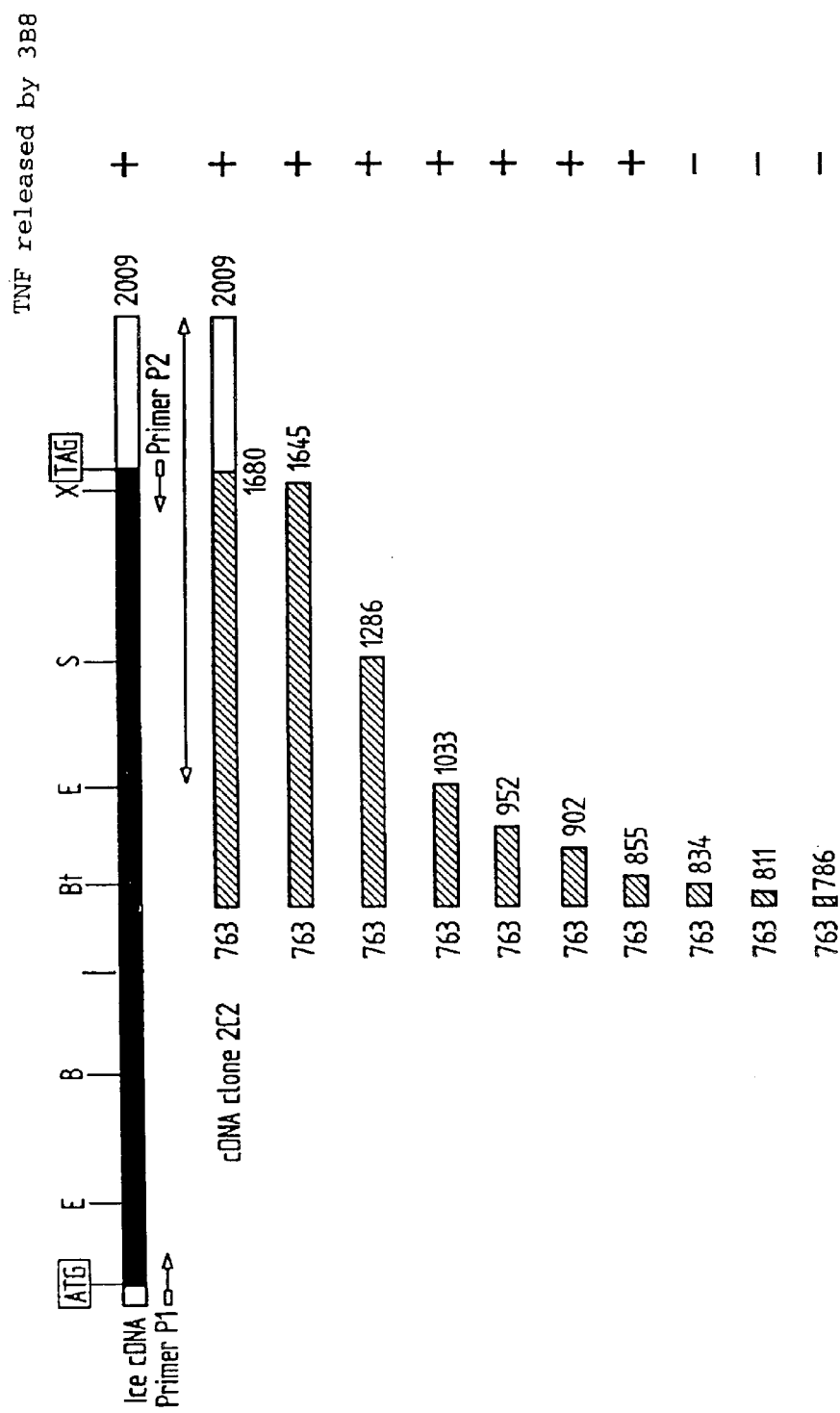

FIG_1A
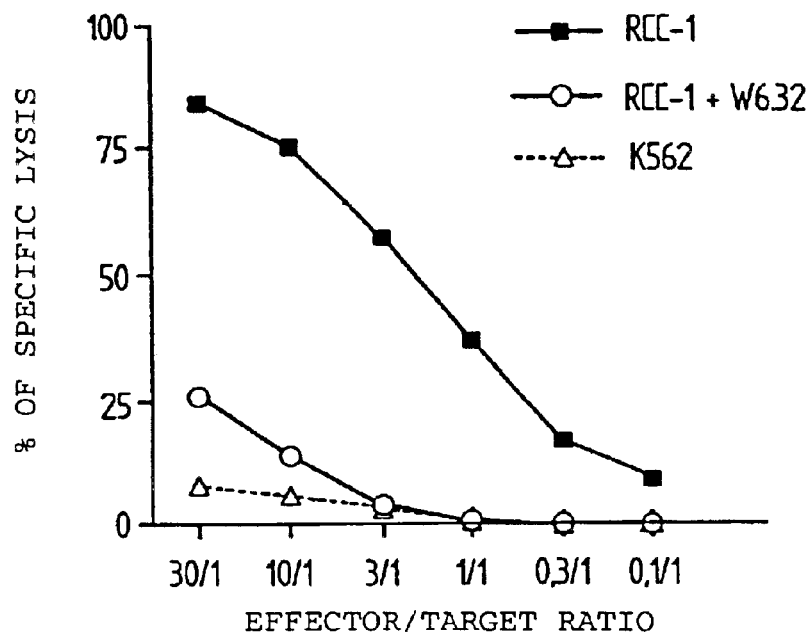
FIG_1B
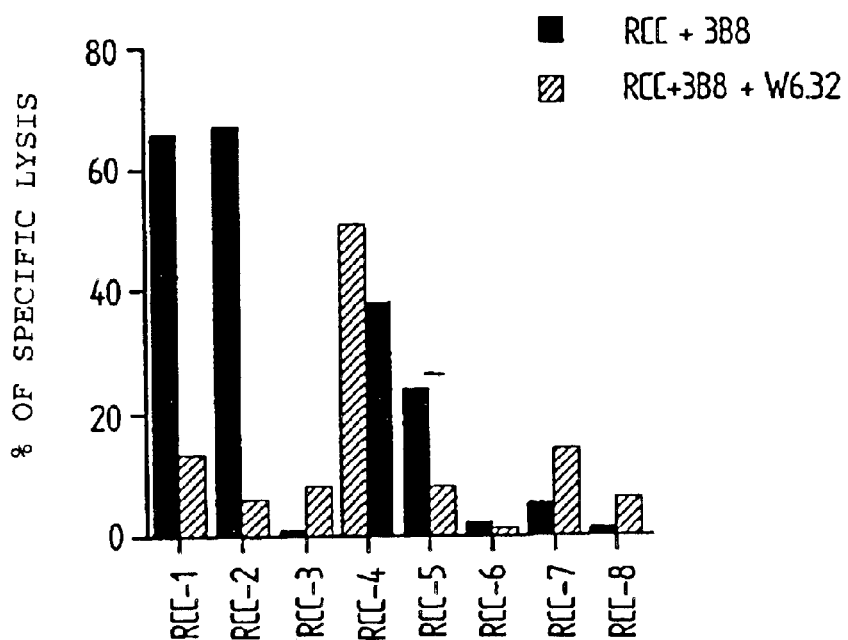

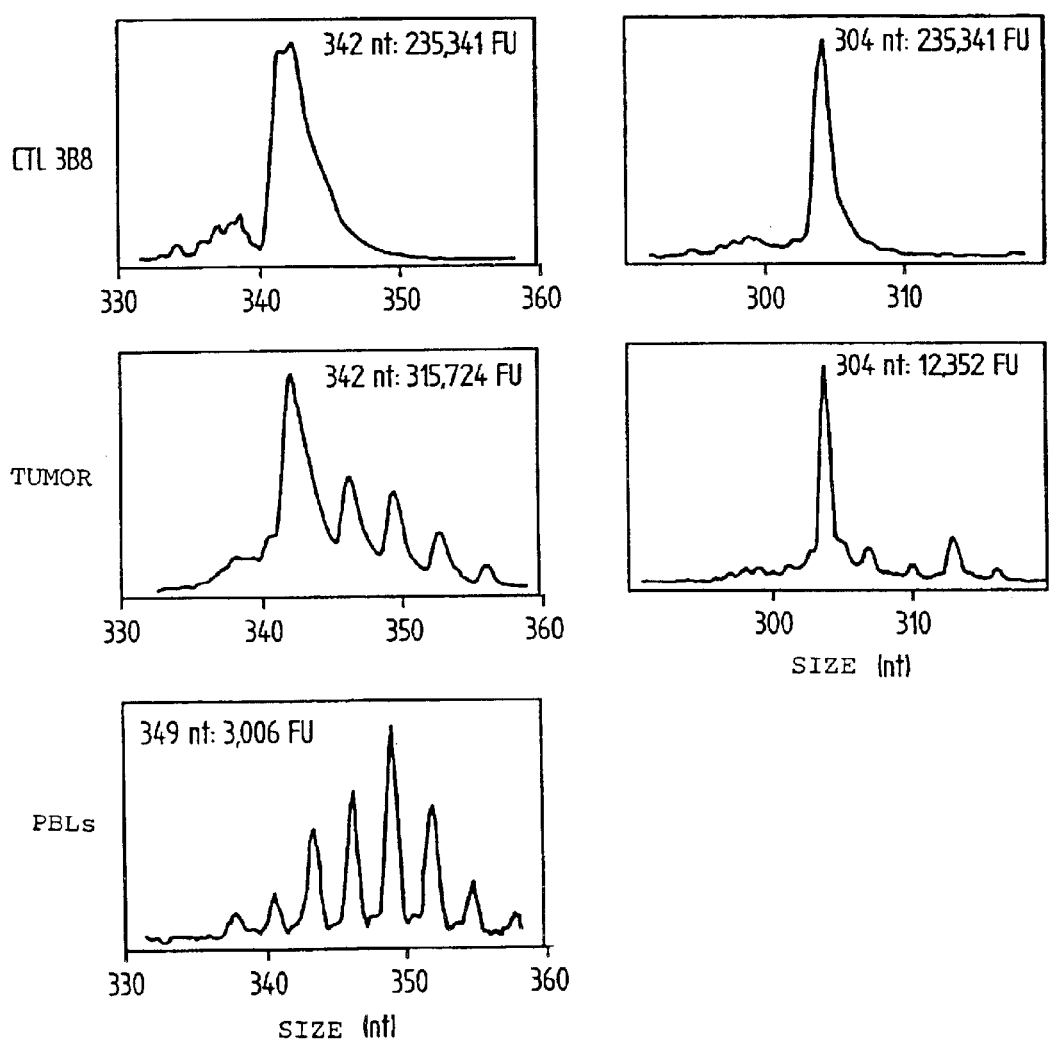

FIG_3
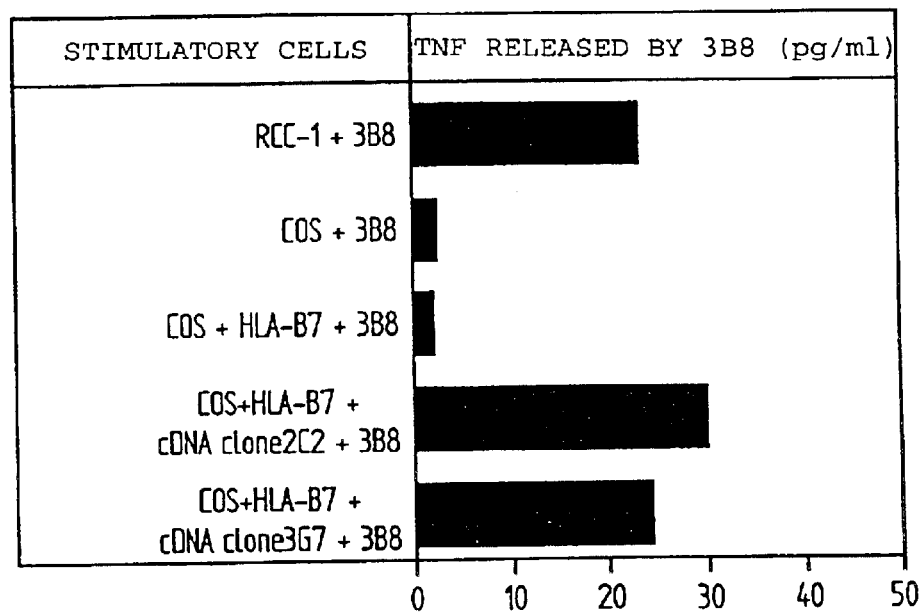

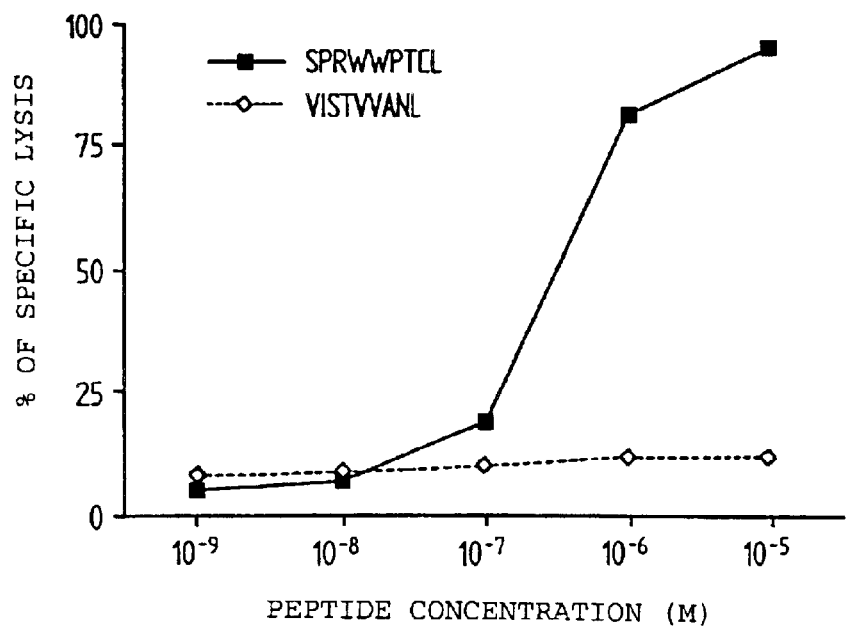
FIG_5
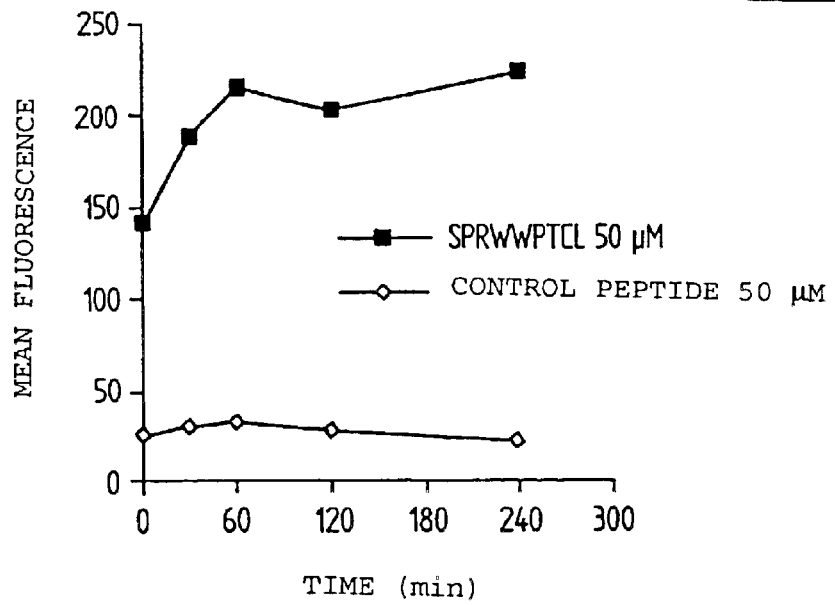
FIG_6

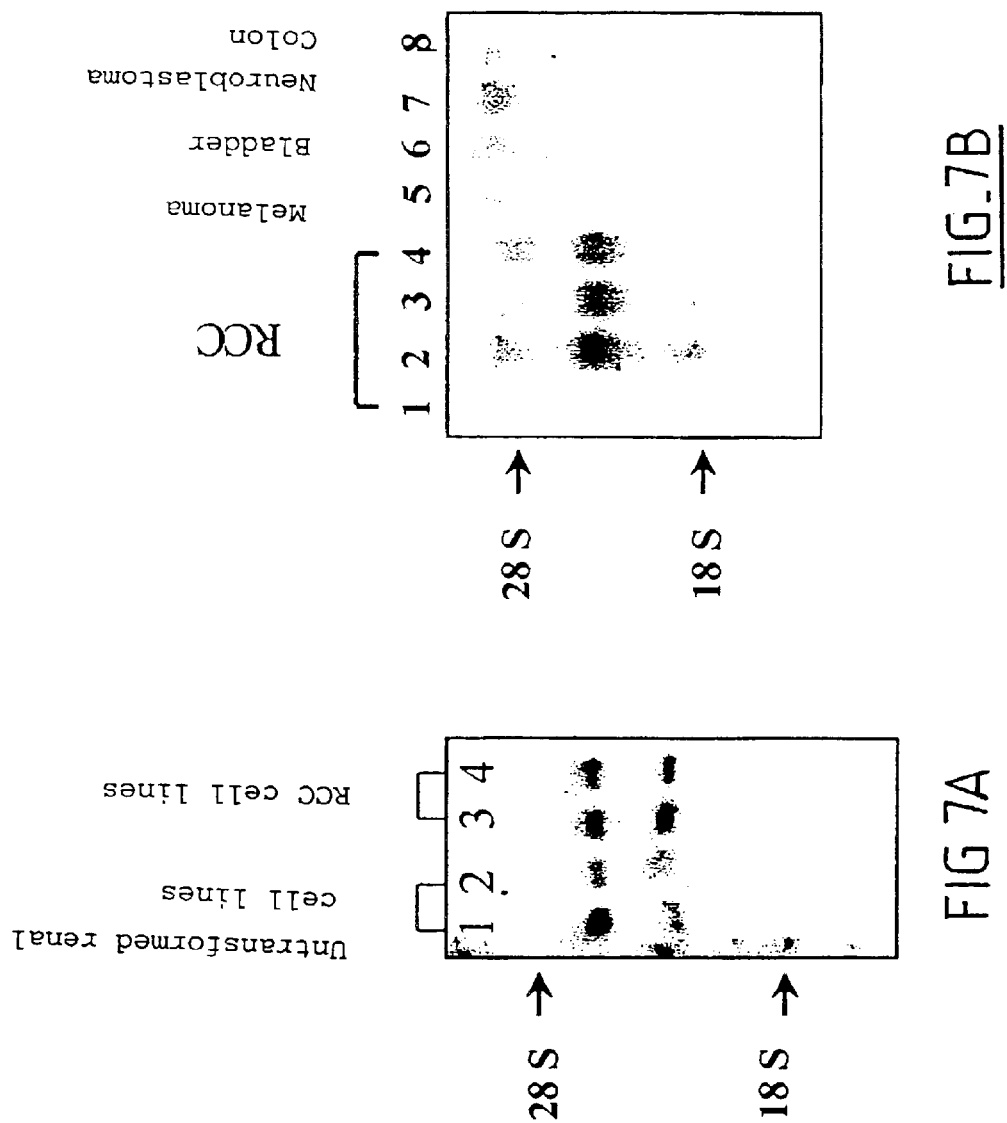

FIGURE 8A

B
atGcggctgcacagacttcgtgccggctgagcgccggtgcctgtgggctttctgctgctt        60
 M  R  L  H  R  L  R  A  R  L  S  A  V  A  C  G  L  L  L  L
cttgtccggggccaggccaggactcagtcagtccatccggaccacacacgggcag            120
 L  V  R  G  Q  G  Q  D  S  A  S  P  I  R  T  T  H  T  G  Q
gtgctggggagtcttgtccatgtgaaggcgccaatgccggggtccaaacctttcctggga      180
 V  L  G  S  L  V  H  V  K  G  A  N  A  G  V  Q  T  F  L  G
attccatttgccaagccaccctctagtccgctgcgatttgcaccccctgagcccctgaa       240
 I  P  F  A  K  P  P  L  G  P  L  R  F  A  P  P  E  P  P  E
tcttggagtggtgtgagggatgaaccaccatccggcatgtgtctacaggacctcacc         300
 S  W  S  G  V  R  D  G  T  T  H  P  A  M  C  L  Q  D  L  T
gcagtggagtcagagtttcttagccagttcaaacatgacctccccttccgactccatgtct    360
 A  V  E  S  E  F  L  S  Q  F  N  M  T  F  P  S  D  S  M  S
gaggactgcctgtacctctcagcatctacacgcccatagccatgaaggctctaacctg        420
 E  D  C  L  Y  L  S  I  Y  T  P  A  H  S  H  E  G  S  N  L
                        F                                    C
ccggtgatggtgtggatccacGgtggtgcgcttgtttttgcatgGcttccttgtAtgAt       480
 P  V  M  V  W  I  H  G  G  A  L  V  F  L  A  W  L  P  C  M  M
                      E                     A  S  L  Y  D
ggttccatgctgcctggagaacgtgcttggtggtCatcatccagtaccgcctgggt         540
 W  C  G  S  T  V  R  L  F  L  A  W  L  P  C  M  M
                         V  I  Q  Y  R  L  G
 G  S  M  L  A  A  L  E  N  V  V  W  S  S  S  T  A  W  V
 V  P  C  W  L  P  W  R  T  W  W  S  S  S  T  A  W  V FIGURE 8A (continued)

```
gtcctgggcttcttcagcactggagacaagcacgcaactgggctacctggac    600
 V  L  G  F  F  S  T  G  D  K  H  A  T  G  N  W  G  Y  L  D
 S  W  A  S  S  A  L  E  T  S  T  Q  P  A  T  G  A  T  W  T
caagtggctgcactacgctgggtcctgggtccagcagaatatcgccactttggaggcaaccctgac    660
 Q  V  A  A  L  R  W  V  Q  Q  N  I  A  H  F  G  G  N  P  D
 K  W  L  H  Y  A  G  S  S  R  I  S  P  T  L  E  A  T  L  T
cgtgtCaccattttttggcgagtctgcggtggcacgagtgtcttcgcttgttgtcc    720
 R  V  T  I  F  G  E  S  A  G  G  T  S  V  S  S  L  V  V  S
 V  S  P  F  L  A  S  L  R  V  A  R  V  C  L  R  L  L  C  P
cccatatcccaaggactcttccacgaagccatcatggagagtggcgcgtggccctcctgccc    780
 P  I  S  Q  G  L  F  H  G  A  I  M  E  S  G  V  A  L  L  P
 P  Y  P  K  D  S  S  T  E  P  S  W  R  V  A  W  P  S  C  P
                                     D  A
ggcctCattgccagctcagctgAtgtCatctcccacggtggtggccaacctgtctgcctgt    840
 G  L  I  A  S  S  A  D  V  I  S  T  V  V  A  N  L  S  A  C
 A  S  L  P  A  Q  L  M  S  S  P  R  W  W  P  T  C  L  P  V
gaccaagttgactctgaggccctgtgggctgcctgcgggggcaagagtaaagaggagatt    900
 D  Q  V  D  S  E  A  L  V  G  C  L  R  G  K  S  K  E  E  I
 T  K  L  T  L  R  P  W  W  A  A  C  G  A  R  V  K  R  R  F
cttgcaattaacaagcctttcaagatgatccccggagttggtggatggggtcttcctgccc    960
 L  A  I  N  K  P  F  K  M  I  P  G  V  V  D  G  V  F  L  P
 L  Q  L  T  S  L  S  R  -
aggcaccccaggagctgctgcctctgccgactttcagcctgtccctagcattgttggt    1020
 R  H  P  Q  E  L  L  A  S  A  D  F  Q  P  V  P  S  I  V  G
```

FIGURE 8A (continued)

```
gtcaacaacaatgaattcggctggctcatcccaaggtcatgaggatctatgataccccag  1081
 V  N  N  N  E  F  G  W  L  I  P  K  V  M  R  I  Y  D  T  Q
aaggaaatggacagagaggcctcccagctgctctgcagaaaatgttaacgctgctgatg   1140
 K  E  M  D  R  E  A  S  Q  A  A  L  Q  K  M  L  T  L  L  M
ttgcctcctacatttgtgacctgctgagggaggagtacattgggacaatggggatccc    1200
 L  P  P  T  F  V  D  L  L  R  E  E  Y  I  G  D  N  G  D  P
cagaccctccaagcgcagttccaggagatgatggcggactccatgtttgtgatccctgca  1260
 Q  T  L  Q  A  Q  F  Q  E  M  M  A  D  S  M  F  V  I  P  A
ctccaagtagcacatttcagtgttcccgggcccctgtgtacttctacgagttccagcat  1320
 L  Q  V  A  H  F  Q  C  S  R  A  P  V  Y  F  Y  E  F  Q  H
cagcccagctggctcaagaacatcaggccaccgcacatgaaggcagaccatggtgatgag 1380
 Q  P  S  W  L  K  N  I  R  P  P  H  M  K  A  D  H  G  D  E
cttcctttgtttcagaagtttctggggcaactacattaaattcactgaggaagag      1440
 L  P  F  V  F  R  S  F  G  G  N  Y  I  K  F  T  E  E  E
gagcagctaagcaggaagatgatgaagtactgggccaactttgcgagaaatgggaacccc 1500
 E  Q  L  S  R  K  M  M  K  Y  W  A  N  F  A  R  N  G  N  P
aatggcgagggtctgccacactggccgcttcgaccaggagcaatacctgcagctg      1560
 N  G  E  G  L  P  H  W  P  L  F  D  Q  E  E  Q  Y  L  Q  L
aacctacagcctgcggtgggccgggctctgaaggcccacagccacgttctgaaggatag  1620
 N  L  Q  P  A  V  G  R  A  L  K  A  H  H  R  L  Q  F  W  K  K
gcgctgccccaaaagatccaggagctcgaggagcctgaagagagacacagagctgtag   1740
 A  L  P  Q  K  I  Q  E  L  E  E  P  E  E  R  H  T  E  L  -
```

PEPTIDE COMPOUNDS DERIVED FROM A SHIFTED ORF OF THE ICE GENE

The present invention relates to a peptide compound which causes a tumor-specific T response, and which comprises a sequence of at least 8 consecutive amino acids of the peptide sequence encoded by a frame-shifted sequence of the iCE gene. The invention also relates to a pharmaceutical composition comprising said peptide compound and to the use of these compounds for manufacturing a medicinal product intended for treating cancer, in particular for treating solid tumors.

Various products turn out to be recognized by T cells which are reactive with respect to tumors, most of them being isolated from patients with melanomas. Some of these antigens (Ag) represent products of nonmutated genes whose expression in normal adult tissues is restricted to the testicles (MAGE-1, MAGE-3, BAGE and GAGE) (1–4). Other nonmutated genes are differentiation antigens which are also expressed, for example, in normal melanocytes, but not in other normal tissues. These differentiation antigens comprise the melanocyte line gene products MART-1/ MelanA (5, 6), gp100 (6), tyrosinase (7, 8) and gp75 (9). T cells which are reactive with respect to melanomas also turn out to recognize mutated products of the α-catenin (10), MUM1 (11) and CDK-4 (12) genes. T cells which are reactive with respect to renal cell carcinoma (RCC) also turn out to recognize products of point-mutated genes such as HLA-A2 (13) or HSP70-2 (14).

In addition, some Ags which are recognized by reactive T cells can be generated by modified transcription products comprising intron sequences, as in the case of MUM-1 (11), N-acetylglucosaminyltransferase-V (GnT-V) (15) or gp100 (16). The T-cell surveillance of cell integrity may focus on peptides encoded by an alternative open reading frame (ORF) located inside the primary ORF, as in the case of gp75/TRP-1 (17) and NY-E50-1 (18). Few examples exist in the literature on the use of alternative ORFs in eukaryotes, and the biological significance of the corresponding products is unknown. However, it may be assumed that these products might be used as antigenic targets, and increase the effectiveness of immune surveillance. Specifically, There is an increasingly clear relationship between the abnormal translational control of gene expression (such as for c-mys or FGF-2) (19–21) and the appearance of cancer, and thus the immunogenic peptides in tumors may originate from peptides which derive from the primary ORF, but also from alternative ORFs.

The screening of a cDNA library with a clone of T cells which are reactive with respect to the HLA-B7-restricted renal cell carcinoma (RCC), and which derive from tumor-infiltrating lymphocytes (TILS) which have been amplified by cloning in vivo, led, in the context of the present invention, to the isolation of a nonamer encoded by an alternative (A+1 frameshift) open reading frame (ORF) of the intestinal carboxylesterase (iCE) gene. This peptide binds to HLA-B*0702-presenting molecules, as determined in a binding assay by immunofluorescence using transfected T2 cells. The constitutive expression of this alternative-ORF protein was observed in all the transformed HLA-B7* renal cell lines which were recognized by TILs in cytotoxicity assays. The iCE gene is transcribed in RCC tumors, as well as in normal liver, intestine and kidney tissues. A mutation in the natural ATG translation start site does not impair recognition, which shows that the frameshift (i.e. sliding the ribosome forward) and the recoding are not the mechanisms involved. In addition, a point mutation in the three AUG codons which can be used as alternative translation start sites in the +1 ORF does not abolish recognition, whereas the mutation of an upstream ACG codon does so, indicating that the latter codon initiates the translation of the alternative ORF. Unexpectedly, this alternative ORF is thus initiated from a non-AUG (ACG) cryptic codon.

DESCRIPTION

Thus, the present invention relates to a peptide compound which leads to a tumor-specific T response, and which comprises a sequence of at least 8 consecutive amino acids of the peptide sequence encoded by the frame-shifted sequence (A+1 or A+2) of the iCE gene. The nucleotide sequence and peptide sequence of iCE (*Homo sapiens* intestinal carboxylesterase; liver carboxylesterase-2) are available on the site www.ncbi.nlm.nih.gov under the access number NM_3869. The publication Schwer, H., Langmann, T., Daig, R., Becker, A., Aslanidis, C. and Schmitz, G. Molecular cloning and characterization of a novel putative carboxylesterase, present in human intestine and liver. Biochem. Biophys. Res. Commun. 233 (1), 117–120 (1997) (MEDLINE 97289502) is incorporated in the description by way of reference.

The invention relates more specifically to a peptide compound which causes a specific T response, characterized in that it comprises a sequence of at least 8 consecutive amino acids of the following sequence SEQ ID No. 1:
TVVRLFLAWLPCMMVPCWLPWRTWW-
WSSSSTAWVSWASSALETSTQPATGATWTK WLHY-
AGSSRISPTLEATLTVSPFLASLR-
VARVCLRLLCPPYPKDSSTEPSWRVAW
PSCPASLPAQLMSSPRWWPTCLPVT-
KLTLRPWWAACGARVKRRFLQLTSLSR.

Mention may be made in particular of a peptide compound which has at least 80% identity with the sequence SPRWWPTCL (SEQ ID No. 2).

The invention also relates to a method for identifying peptide compounds comprising a sequence which has at least 80% identity with a sequence of approximately 9 to 10 consecutive amino acids of the sequence SEQ ID No. 1, characterized in that it comprises the following steps:
  a) Determining fragments which possess a sequence of approximately 9 to 10 amino acids comprising an anchoring motif for a given HLA molecule,
  b) determining the immunogenicity of the peptide fragments obtained in step a), preferably by carrying out an Elispot assay.

A subject of the invention is the peptide compounds which can be obtained from this method.

The peptide fragments to be assayed can be easily obtained by chemical synthesis based on general knowledge in the technical field.

The Elispot assay is widely described in the documents of the prior art. For example, Herr et al, (1998) relates to an Elispot method for detecting and quantifying CD8+T lymphocytes which secrete TNF-α. In summary, MultiScreen-HA plates (Millipore, Bedford, Mass.) are covered with an anti-TNF-α antibody (clone 195; Boehringer Mannheim) and CD8+T lymphocytes are added in the presence of antigenic peptides. The secreted TNF-α is detected with a rabbit anti-TNF-α antibody (Serotec, Oxford, UK), a biotin-coupled rabbit anti-IgG antibody (Boehringer Mannheim) and the biotin-avidin-peroxidase complex (Vector, Burlingame, Calif.). The number and the surface area of the areas where the cytokine is present are determined automatically by computer, (Herr et al, 1997). Other documents, such as Herr et al, (1996) materials and methods section paragraph 2 pages 132 to 135, and Scheibenbogen et al, (1997) page 933, describe this method and are also incorporated in the description by way of reference.

In addition, the invention relates to a method for revealing artificial point modifications or mutations which are capable of increasing the immunogenicity of the peptide compounds described above, said method comprising the following steps:

a) Determining fragments which possess a sequence of approximately 9 to 10 amino acids comprising an anchoring motif for a given HLA molecule, b) introducing an additional point modification (for example a post-translational modification) or mutation at residues 4, 5, 6, 7 or 8, c) determining the immunogenicity of the peptide fragments obtained in step b), preferably by carrying out an Elispot assay.

This method is well known to persons skilled in the art. It is possible in particular to incorporate into the description, by way of reference, the teachings which are to be found at the following Internet address: www.bimas.dcrt.nih.gov/molbio/hla_bind/

This method makes it possible to determine any artificial (not present in human tumors) point modification or mutation which is thought to be capable of improving the active principle (the immunogenic mutated peptide), using the so-called "reverse immunology" method. Based on the knowledge of the amino acid sequence of a protein, it is possible to predict which of the peptides are capable of binding to an HLA pocket regardless of its specificity (HLA-A2, HLA-A1, HLA-B7, etc.), then to test these peptides in vitro for their capacity to effectively bind to the HLA allele under consideration, and then to introduce a point modification or mutation on the amino acids in certain positions which are critical for affinity. The BIMAS computer program makes it possible to obtain such a prediction. The general rules concerning the amino acids involved in anchoring to HLA molecules are set out in Parker et al, (1992 and 1994) and Rammensee et al, (1995). This information is incorporated into the description by way of reference. Of course, the method according to the invention is not limited to the use of the BIMAS program, and can be implemented with any equivalent program.

In another aspect, a subject of the invention is a peptide compound which can be obtained using a method mentioned above, characterized in that it comprises a sequence of approximately 9 to 10 amino acids of the sequence SEQ ID No. 1 which has at least one mutation or one modification with respect to the sequence SEQ ID No. 1, and in that it causes a specific T response. Such a peptide compound can in particular be derived from the sequence SPRWWPTCL (SEQ ID No. 2).

In the context of the invention, the term "peptide compound" is intended to mean an entity which consists of a minimum of one peptide fragment derived from the polypeptide encoded by an A+1 or A+2 alternative ORF of iCE, or of a series of said peptide fragments, and which optionally has one or more other elements other than natural or unnatural amino acids. The aim of these elements is to chemically or physically protect said peptide fragments, and/or to promote their absorption by the body and/or their administration and/or their bioavailability. For example, this protection enables the peptides to reach their targets without suffering the action of various proteases which are present in the body. Such chemical modifications may also increase the affinity of an antigenic peptide for HLA-A2 molecules and enable increased effectiveness of the vaccine in vivo to be obtained, Rosenberg et al, (1998).

Said elements can be, for example:

Protective chemical groups which are known to persons skilled in the art and which react with the NH2 and/or COOH ends of a peptide, this modification not significantly decreasing the immunogenic nature of the peptide.

Chemical groups which improve the effectiveness of the vaccine in vivo.

Lipids or fatty acids which are covalently bonded to the peptide fragments so as to form peptide compounds which are termed lipopeptides. Palmitic acid is one example among others, Vitiello et al, (1995), which has been incorporated into the description by way of reference.

A carrier protein for said peptide fragments which possesses restriction sites and enables the intact peptide fragments to be conveyed to their sites of action in the body.

Thus, the peptide compound according to the invention can comprise at least one element other than natural amino acids.

An additional embodiment of the invention relates to a DNA fragment encoding at least one peptide fragment defined above. This fragment can comprise a sequence which has at least 50% identity with a sequence of at least 24 consecutive nucleotides of the following sequence SEQ ID No. 3:

acggtggtgcgcttgtttttggcatggcttccttgtatgatggttccatgctggc tgccttggagaacgtggtggtggtcatcatccagtaccgcctgggtgtcctgggc ttcttcagcactggagacaagcacg-caaccggcaactggggctacctggaccaag tggctgcactacgctgggtc-cagcagaatatcgcccactttggaggcaaccctga ccgtgtcaccatttttg-gcgagtctgcgggtggcacgagtgtgtcttcgcttgtt gtgtcccccatatcccaaggactcttc-cacggagccatcatggagagtggcgtgg ccctcctgcccggcctcattgc-cagctcagctgatgtcatctccacggtggtggc caacctgtctgcctgtgac-caagttgactctgaggccctggtgggctgcctgcgg ggcaagagtaaagaggagattcttg-caattaacaagcctttcaagatgatccccg gagtggtggatggggtcttcct-gccc This sequence corresponds to the A+1 alternative ORF of the iCE gene which is expressed in tumor cells. The expression product of this ORF is recognized by a clone of T cells which are reactive with respect to the HLA-B7-restricted RCC. The reactive TILs are amplified in situ in the tumor site.

The term "DNA fragments" is intended to mean single-stranded or double-stranded DNA, cDNA and/or RNA fragments. The nucleotide sequence corresponding to the amino acid sequence of said peptide fragments can vary so as to comprise all the various possible codons for a given amino acid according to the principle of degeneracy of the genetic code. A subject of the present invention is also a vector for expressing a peptide fragment, containing an abovementioned DNA fragment fused to a promoter which is strong and effective in eukaryotic cells and/or in prokaryotic cells, in particular in human cells. The vector can be viral, a plasmid vector or a pseudovector, and can comprise selection markers and express immunological adjuvants such as cytokines and/or lymphokines.

The invention also relates to dendritic cells loaded with peptide compounds and dendritic cells transformed with the expression vector expressing the peptide fragments. These cells can also be macrophages. Nestle et al, (1998), describe a vaccination method which consists in loading the dendritic cells taken from a patient with antigenic peptides (in culture in vitro) and injecting them into the lymphatic system of this same patient. This publication is cited in the description by way of reference.

The subject of another aspect of the invention is a pharmaceutical composition comprising a peptide compound or a mixture of peptide compounds according to the invention and a pharmaceutically acceptable vehicle. This composition can also comprise one or more immunological adjuvants, in particular factors which are cytotoxic for tumors.

The invention also relates to a pharmaceutical composition comprising an expression vector as mentioned above and a pharmaceutically acceptable vehicle, or a DNA fragment according to the invention, or alternatively the cells indicated above, and a pharmaceutically acceptable vehicle.

The pharmaceutical composition or the combination product according to the invention can also comprise one or more immunological adjuvants, in particular agents which are cytotoxic for tumors. These products can comprise a pharmaceutical vehicle which is compatible with IV, subcutaneous, oral or nasal administration, and which is preferably selected from positively or negatively charged liposomes, nanoparticles or lipid emulsions.

Another aspect of the invention relates to the use of a peptide compound as defined above for manufacturing a medicinal product in particular intended for the treatment of cancer, in particular solid tumors, especially carcinomas, melanomas, neuroblastomas, preferably hepatocarcinomas and adenocarcinomas of the colon or of the kidney. This medicinal product may be intended for immunization ex vivo, which consists in particular in inducing tumor-specific CTLs in vitro, expanding them and reinjecting them, said induction possibly being carried out with the aid of loaded dendritic cells or with an immunization in vivo. The invention also relates to the use of said peptide compound for increasing, in culture medium, the CTL population of tumors and/or inducing the secretion by said CTLs of cytotoxic factors such as, for example, IL-2, IFN-γ and TNF, and/or for stimulating immune defenses, in particular to increase the CTL population of tumors and/or to induce the secretion by said CTLs of cytotoxic factors such as, for example, IL-2, IFN-γ and TNF.

In an additional embodiment, the invention relates to a method for producing an antibody which recognizes a previously described peptide compound, comprising the steps consisting in:
a) Immunizing a mammal with said peptide compound,
b) isolating a monoclonal antibody which binds to said peptide in an immunological assay.

The invention is also directed toward a monoclonal antibody which can be obtained using this method.

The invention is also directed toward a method for detecting a peptide or polypeptide encoded by the A+1 ORF of iCE, comprising the steps consisting in:
a) Bringing a sample removed from an individual into contact with an abovementioned monoclonal antibody,
b) allowing the formation of the peptide or polypeptide/ antibody complex,
c) detecting said peptide or polypeptide by means of a detectable label which is in the complex or which binds to the complex;
and a diagnostic kit comprising in particular said antibody for detecting cancer, in particular for the prognostic of existing cancer in an individual. A composition comprising in particular said monoclonal antibody and a pharmaceutically acceptable vehicle may also be useful in the context of the cancer treatment.

The iCE cDNA was isolated originally from a human small intestine cDNA library (31). It exhibits 65% homology with other carboxylesterases of various mammalian species. It is expressed in human intestine, liver and kidney, and appears to play an important role in xenbiotic control and detoxification of the intestinal mucosa (31). A large series of T-cell epitopes encoded in the minimum nucleotide region of the regular iCE ORF was tested, and none of them were recognized in the context of the class I HLA-B*0702- restricted element.

Conversely, a 453-nt ORF encoded in this region following a +1 frameshift turned out to encode a nonamer with HLA-B7-anchoring residues at positions 2, 3 and 9 (SPRWWPTCL, SEQ ID No. 2). A semi-maximal lysis was obtained with less than $10^{-6}$ M of nonapeptide in target sensitization assays. The binding of this nonapeptide to T2 cells transfected with HLA-B*0702 is stable with time, suggesting that low amounts of expression of this alternative ORF are sufficient to induce T-cell recognition in vitro and T-cell proliferation in vivo, as shown, in the latter case, by the in situ amplification at the tumor site of the corresponding TIL subpopulation.

The results obtained in the context of the invention reveal that a novel mechanism is involved in the generation of T-cell epitopes. An alternative ORF induced by a non-AUG cryptic codon which leads to a +1 translational reading frame has proved to encode a tumor Ag recognized by TILs. In two other examples, gp75/TRP-1 (17) and NY-E50-1 (18), peptides recognized by TILs are encoded by an alternative ORF located within the primary ORF. A mechanism by which the alternative ORF is translated has been suggested for gp75/TRP-1 (17), for which recognition is affected by the presence of an internal AUG preceding the epitope. In addition to this ribosomal screening mechanism, a ribosomal frameshift (39, 40) has been suggested for the production of T-cell epitopes (41), but, in the case of the iCE gene, this possibility is excluded since mutating the natural ATG translation start site does not affect peptide recognition. In fact, the presence of the first cryptic internal translation start site (an ACG codon at position 440) in the +1 alternative ORF of iCE is sufficient to direct the expression of sufficient amounts of iCE peptide for the activation of T cells in vitro, as well as in vivo (i.e. leading to clonal expansion of T cells in situ). The leaky screening model, in which ribosomes occasionally avoid the first AUG which has a mediocre Kozak consensus sequence and initiate a translation on a downstream AUG, may apply to iCE due to the presence of a pyrimidine at position +4 in place of a purine.

To our knowledge, this is the first example of an epitope which is encoded by a non-ATG-defined alternative ORF and recognized by T cells with tissue reactivity, in a human disease. Nontransformed HLA-B7+renal cell lines, which have been established in vitro, have been recognized in cytotoxicity assays by the TIL-derived clone 3B8. It has been shown that alternative translation initiations of the fiberblast growth factor 2 molecule which are not ATG- defined are induced in stressed or transformed cells, in comparison with those which are ATG-defined (20). Similarly, the expression of non-ATG-initiated forms of iCE can be regulated positively in tumors, leading to the clonal expansion in situ of the corresponding TILS. This alternative ORF of iCE thus expresses a novel tumor Ag which is advantageous for use in immunotherapy, in particular in patients with a hepatocarcinoma or adenocarcinoma of the colon or of the kidney. More generally, the results obtained show the possibility that alternative ORFs induced by non- AUG codons in the 3 translational reading frames may encode T-cell epitopes in certain human diseases such as cancer or autoimmune disorders.

For the remainder of the description, reference will be made to the legends of the figures presented below.

LEGENDS

FIG. 1:
(A) Specific Lysis of the Autologous RCC-1 Cell Line by CTL Clone 3B8.

The cytotoxicity of clone 3B8 with respect to the autologous RCC-1 cell line and to K562 cells was tested in a standard chromium release assay at various E:T ratios. Blocking of the lysis with the mAb W6.32 is also represented.

(B) Cytotoxicity of 3B8 with Respect to Various Allogenic Cell Lines.

3B8 was tested with the autologous RCC-1 line and various allogenic RCC cell lines (RCC-3, RCC-4 and RCC-5) in a standard chromium assay at an E:T ratio of 18:1. By way of control, the mAb W6.32 was used to block class I HLA molecules which are involved in antigen presentation.

FIG. 2: Size analysis of CDR3 in TILs and in clone 3B8 using selected primers TCRBV (A) and TCRBJ (B).

The RNA was subjected to reverse transcription and amplification over 40 cycles using the primers TCRBV5 and BC. The DNA obtained was copied over 5 cycles in an elongation reaction using the nested fluorescent primer TCRBC (A) or TCRBJ152 (B) (13 BJ primers tested, BJ1S1-BJ1S7, BJ2S1-BJ2S6). The amplified products were analyzed on an automated sequencer. The profiles obtained show the sizes in nt (x axis) and the intensity of fluorescence (y axis) of the amplified products. The absolute FU values obtained for the dominant peaks are indicated.

FIG. 3: Stimulation of CTL clone 3B8 by COS-7 cells transiently cotransfected with the expression vector pcDNAI containing the 2C2 or 3G7 cDNA clone and the autologous HLA-B*0702 cDNA.

The control stimulating cells comprise the RCC-1 cell line, which is used as a positive control, and COS-7 cells transfected with the HLA-B*0702 cDNA alone, which are used as a negative control. The iCE cDNA was transiently cotransfected into COS-7 cells with the HLA-B*0702 cDNA, and clone 3B8 was added after 48 hours. TNF production was determined by its cytotoxic effect on WEHI cells, 18 hours later. The control stimulating cells comprise the RCC-1 cell line, which is used as a positive control, and COS-7 cells transfected with HLA-B*0702 alone, which are used as a negative control.

FIG. 4: Location of the iCE cDNA sequence encoding the antigenic peptide recognized by 3B8.

This is a schematic representation of the full length iCE cDNA sequence, of the cDNA 2C2 clone and of various truncated 2C2 cDNAs. The untranslated 5' and 3' regions are represented by outlined boxes. The translated sequence of human iCE is represented by a filled-in box; the cDNA clone 2C2 is represented by a dotted box and the truncated 2C2 cDNAs are indicated by hatched boxes. The nucleotides are numbered starting from the natural ATG nonsense codon. The small black frames with an arrow indicate the position of the P1 primer and of the P2 primer. The cDNA used as a probe for hybridizing the RNA transfer is indicated by a two-tipped arrow. Restriction sites (B: Bam HI; Bs: BstX I; E: EcOR I; S: Sma I; X: Xba I). The recognition, by CTL clone 3B8, of COS-7 cells transiently transfected with the autologous HLA-B*0702 cDNA and with various truncated cDNAs is indicated. The transfected cells were incubated for 24 hours with 5000 3B8 cells, and the amount of TNF in the supernatants was measured via the cytotoxicity effect on WEHI-13 cells.

FIG. 5: Lysis, by CTL clone 3B8, of autologous EBV-transformed cell lines incubated with the iCE encoded peptide.

2000 EBV-transformed cells were incubated and labeled with 51Cr for 1 h in the presence of the HLA-B7-restricted iCE peptide (SPRWWPTCL; SEQ ID NO:2) or another control HLA-B7-restricted peptide (VISTVVANL; SEQ ID NO:9). Clone 3B8 was then added as an effector, in a ratio set at 30:1. Chromium release was measured after 4 h.

FIG. 6: Induction of HLA-B7 expression on T2 cells by the iCE peptide.

T2 cells were incubated at 26° C. for 16 hours in medium without serum containing peptides at a concentration of 50 $\mu$M. Then, the peptides were again added, and the cells were incubated at 37° C. At 30-min or 1-h intervals, aliquots of cells were harvested, and the change in HLA-B7 expression was monitored by flow cytometry using an anti-HLA-B7 mAB (HB59). By way of control, an HLA-A2-restricted HSP70 peptide was used. The peptide SPRWWPTCL is provided in SEQ ID NO: 2.

FIG. 7: Analysis of iCE RNA transcription products in various cell lines (A) and various tumor fragments (B).

5 $\mu$g of poly(A)+ RNA (A) and ten $\mu$g of total RNA (B) were loaded onto a denaturing formaldehyde gel containing 1% of agarose. The RNA was transferred onto a membrane, and the RNA transfer was hybridized with a 32P-labeled fragment of cDNA clone 2C2, which has been used as a probe. Hybridization was carried out with a glyceraldehyde-3-phosphate dehydrogenase (GAPDH) probe as an internal control for loading equal amounts of RNA for the analysis (not represented).

FIG. 8: A non-ATG-defined open reading frame of iCE is recognized by the CTL clone 3B8.

(A) Sequence of the iCE cDNA coding region (SEQ ID NO:6) with the primary (SEQ ID NO:7) and alternative (SEQ ID NO:8) (a+1 shift) open reading frames. The positions of the mutated nucleotides (nt) are represented in bold capital letters, the corresponding codons are underlined and the position of the mutants A–F tested (B) is indicated above the mutant codons. The sequence of the antigenic peptide encoded by the +1 ORF is underlined.

(B) The ability of point mutants (A–F) to stimulate TNF release from clone 3B8 after cotransfection with HLA-B*0702 in COS cells was tested. The negative controls comprise a simulated transfection with HLA-B*0702 or the iCE cDNA alone, or a cotransfection with HLA-B*0702 and a pcDNAI control plasmid.

EXAMPLE 1

Materials and Methods

Cell Lines

K562 cells were cultured, and the B cell line originating from patient 1 which was transformed by EBV in medium consisting of RPMI (Gibco-BRL, Paisley, GB) supplemented with 1% of 200 mM L-glutamine, 1% of 200 mM sodium pyruvate, 1% of Hepes, 5% of fetal calf serum (FCS) and 50 IU/ml of penicillin (Gibgo-BRL, Paisley, GB) was obtained. WEHI-164 clone 13 (W13) and COS-7 cells were cultured in RPMI (Seromed, Biochrom KG, Berlin) supplemented with 1% of 200 mM L-glutamine, 1% of 200 mM sodium pyruvate, 1% of Hepes, 5% of fetal calf serum (FCS) and 50 IU/ml of penicillin.

Patients and Establishment of RCC Cell Lines

The RCC cell lines were established as previously described (22). Primary tumors were obtained from untreated patients who had undergone a radical nephrectomy. The RCC-1 cell line was established from patient 1 (HLA A1, A32, B7, B12–44, Cw5, Cw7), this patient being a 56-year-old man with a clear and granular renal cell carcinoma without metastases. After surgery, fragments were treated by enzymatic digestion, and the tumor cell suspensions were cultured in complete RCC medium (22). The RCC-2 (HLA A1, A3, B7, B8, Cw7, Cw7), RCC-3 (HLA A1, A29, B22, B15–62/63, Cw1, Cw7–17), RCC-4 (HLA A3, A19–29, B7, B12–44, Cw7, Cw16), RCC-5 (HLA A1, A3, B6, B22–56, Cw1, Cw7), RCC-6 (HLA A9–24, A32, B12–44, B18, Cw5, Cw5), RCC-7 (HLA A1, A28–68, B8, B40–60, Cw3, Cw7) and RCC-8 (HLA A2, A10–25, B18, B13, Cw8, Cw6) tumor cell lines which derive from the primary tumor of patients 2, 3, 4, 5, 6, 7 and 8, respectively, were maintained in complete RCC medium.

Generation of CTLs from TILs of Patient 1

Autologous TILs were generated from a thawed suspension of dissociated tumor cells. An autologous mixed lymphocyte/tumor cell culture (MLTC) was prepared as follows: on day 1, dissociated tumor cells were seeded in a proportion of $2\times10^6$ TILs in 6-well flat-bottomed plates (Falcon, Becton Dickinson, New Jersey) in RPMI 1640 (Gibco-BRL, Paisley, GB) containing 1% of 200 mM L-glutamine, 1% of 200 mM sodium pyruvate, 8% of human AB serum (Institut Jacques Boy, S. A., Reims, France) and 50 IU/ml of penicillin, supplemented with 5% of T-cell growth factor (TCGF) and 50 IU/ml of human interleukin-2 (rIL-2) (Roussel Uclaf, Romainville, France), hereafter termed "MLTC complete medium". The MLTC complete medium was discarded every three days as required, and was replaced with fresh MLTC complete medium. On days 7, 15 and 21, $2\times10^6$ TILs were restimulated with $2\times10^5$ irradiated (100 Gray) autologous tumor cells seeded in 6-well flat-bottomed plates with MLTC complete medium. On day 15, the cytotoxic activity of the TILs was tested against the autologous RCC-1 and K562 cell lines, the surface phenotype was characterized by direct immunofluorescence and the cells were cloned by the limiting dilution technique. The TILs were seeded in a proportion of 0.6 to 600 cells/well in V-shaped 96-microwell plates (Nunc, Denmark) which had been seeded beforehand with irradiated autologous tumor cells ($1\times10^4$/well) as stimulators, and irradiated allogenic PBLs ($8\times10^4$/well) and irradiated EBV-transformed B cells ($2\times10^4$/well) as feeder cells, in a total volume of 200 μl of MLTC complete medium. Every 3 days, 60 μl of supernatant was removed from each well and replaced with 60 μl of fresh medium. The cycotoxicity of the clones was determined in a 4-h standard chromium release assay. Every 7–10 days, CTL clones were restimulated with the allogenic feeder cell line and the autologous tumor cell line, as described above.

Cytotoxicity Assay

The cytolytic activity of the CTLs was determined in a standard $^{51}$Cr release assay as previously described (22). Target cells (RCC and K562 cell lines) were labeled for 1 h with 50 μCi to 100 μCi of $^{51}$Cr (Du Pont, NEN, Boston, Mass.) at 37° C., and $2\times10^3$ cells were seeded in 96-microwell plates in 100 μl of RPMI supplemented with 5% of FCS. Effector cells were added to the wells at various E:T ratios ranging from 40:1 to 0.1:1. For the lysis inhibition with mAbs, target cells were preincubated for 2 h in the presence of a saturating concentration of mAb before adding the effector cells. The 96-microwell plates were incubated at 37° C. for 4 h, and $^{51}$Cr release was determined in the harvested supernatants. For the blocking of cytotoxicity or the production of TNF, the following mAbs were used: W6/32, which is a pan-class I MHC mAb, and B1.23.2 (ME1), which is an HLA-B/C-specific mAb.

Transfection of COS-7 Cells and Screening of Transfection Products

Transfection experiments were carried out with COS-7 cells using the DEAE/dextran/chloroquin method (5, 7, 23). Three days before transfection, COS-7 cells were seeded in 96-microwell flat-bottomed plates, in a proportion of $5\times10^3$ cells/well, in 150 μl of RPMI containing 20% of FCS. The transfection experiments were carried out in duplicate in two different microwell plates. For the transfection, the medium was discarded and then replaced with 30 μl of transfection mixture containing 35 μg of DEAE/dextran (Sigma) and 0.1 mM of chloroquin (Sigma), with 100 ng of plasmid DNA representing a group of approximately 200 recombined clones originating from the cDNA library and 100 ng of the autologous HLA-B*0702 plasmid. The COS-7 cells were incubated for 4 h at 37° C., and then the medium was removed and the cells were incubated for 2 minutes in a 1×PBS buffer containing 10% of dimethylsulfoxide solution. The cells were washed once in 1×PBS buffer, and were incubated with RPMI containing 10% of FCS for 2 days. After 2 days, the ability of the transfected COS-7 cells to stimulate TNF production by clone 3B8 was tested, as determined by the WEHI assay.

The ability of the transfected COS-7 cells to stimulate TNF production was tested (24). $2\times10^3$ CTLs (clone 3B8) were added to 96-microwell flat-bottomed plates containing transiently transfected COS-7 cells in 100 μl of RPMI containing 10% of FCS. 18 h later, each supernatant was harvested, and its TNF content was determined by assaying its cytotoxic effect on WEHI-164 clone 13 cells (25) in a colorimetric assay with 3-[4,5-dimethylthiozol]-2,5-diphenyltetrazolium bromide (MTT).

CDR3 Size Analysis

The size analysis of CDR3 of TCRBV gene segments which are expressed by the CTL clone 3B8, or which are found in blood or tumor fragments, was carried out as previously described (22). The procedure used for the CDR3 size analysis comprises independent RT-PCR amplifications of TCRBV-BC fragments (26), followed by a "flow" of the PCR products using TCRBC or TCRBJ fluorescent nested primers (27) and determination of fluorescent flow product size by electrophoresis on an ABI 373 automated DNA sequencer (Applied Biosystems, Inc. Foster City, Calif.) using the Immunoscope program (28). Since the 5' and 3' primer positions are fixed, variations in size of the flow products are due only to differences in length of the CDR3 regions. Each peak is characterized by its position (CDR3 size) and an intensity of fluorescence (arbitrary fluorescence units or FU). The diagrams representing CDR3 size motifs are calibrated at 100% for the highest peaks. In blood originating from healthy donors, most of the profiles which reflect CDR3 size diversity in a given Vβ subfamily exhibited 5 to 8 peaks 3 nucleotides apart, with an almost Gaussian distribution (21). The dominant peaks were defined as being very strong signals, with a considerable decrease in the other CDR3 signals.

Construction of the cDNA Library

The poly(A)+ RNA was extracted from the RCC-1 cell line using a Maxi Message Marker® kit (R&D Systems, Abingdon, GB), following the manufacturer's instructions. The first strand cDNA was synthesized with the Superscript Choice System® (Gibco BRL, Gaithersburg, Md.) using an oligo-dT primer containing a Not I site at its 5' end, and then the second strand cDNA was synthesized. Semi-Bst XI linkers (InVitrogen) were ligated onto the blunt end of the cDNAs, and then digested with Not I and fractionated by chromatography on Sephacryl S-500 HR columns. cDNA fractions were subcloned into the Bst XI and Not I sites of the expression vector pcDNAI. The recombined plasmids were subjected to electrophoresis in *E. coli* MC1061/P3, and the bacteria were selected on LB agar plates with 50 µg/ml of ampicillin and 10 µg/ml of tetracycline. In the screening experiments, the RCC-1 cDNA library was divided into 400 groups of 200 cDNA clones. Each group of bacteria was amplified, and the plasmid DNA was extracted using the alkaline lysis method (29).

Isolation of the Full Length iCE cDNA and of iCE cDNAs which are Mutated by Point Mutation or Truncated.

The total RNA was extracted from an RCC cell line using the guanidine isothiocyanate/cesium chloride centrifugation procedure (30). A reverse transcription was carried out on 5 µg of total RNA in a 20 µl reaction volume using the cDNA Cycle® kit, following the manufacturer's instructions. 1 µl of the cDNA reaction mixture was used in a PCR reaction using Taq DNA polymerase (Perkin Elmer). For amplifying human iCE cDNA (31), the following primers were used:

Primer P1, 5'-CCCAAGCTTGGTGAATAGCAGCGTGTCCGC-3' (nucleotides 28 to 48, sense, SEQ ID No. 4).

Primer P2, 5'-TGCTCTAGAAGGGAGCTACAGCTCTGTGTG-3' (nucleotides 1666 to 1687, antisense, SEQ ID No. 5).

The conditions for the PCR are as follows: 10 min at 95° C., followed by 30 amplification cycles (94° C. for 1 min, 60° C. for 2 min, 72° C. for 3 min, with a final extension for 10 min at 72° C.).

The PCR product thus obtained is then digested with Hind III and Xba I and is subcloned into the Hind III and Xba I sites of the expression vector pcDNAI for sequencing. The published sequence of the iCE cDNA carries the access number Y09616. iCE mutants were obtained by site directed mutagenesis by encoding the desired point mutation in overlapping oligonucleotide primers and generating the mutants by PCR (32). Sequencing of the PCR products was carried out with an ABI PRISM DNA sequencing kit (PE Applied Biosystems).

Northern Blot Analysis

The total RNA was extracted from various primary tumors using a guanidinium isothiocyanate/cesium chloride centrifugation technique (30). The poly(A+) RNA was prepared as described above from RCC cell lines and from nontransformed renal cell lines. 5 µg of poly(A)+ RNA or 10 µg of total RNA were subjected to electrophoresis in a formaldehyde gel containing 1.2% of agarose, and were transferred onto Hybond-N+ nylon membranes (Amersham, GB). The transferred RNA was hybridized both with a fragment of 2C2 cDNA corresponding to nucleotides 1033 to 2009 of the published human iCE cDNA sequence (31) and with a glyceraldehyde-3-phosphate dehydrogenase (GAPDH) cDNA, as probes. All the probes were labeled with alpha[$^{32}$P]dCTP (3000 Ci mmol-1) using the Prime-IT™ II random primer labeling kit (Stratagene, La Jolla, Calif.). The hybridization was carried out at 48° C. for 16 hours.

The membranes were washed twice with 2×SSC at 52° C. and once for 15 minutes with 0.2 SSC/0.1% SDS, and then they were autoradiographed or analyzed with a Phosphor-Imager (Molecular Dynamics, Sunnyvale, Calif., USA).

EXAMPLE 2

An RCC-specific CTL Clone was Isolated from the TILs

TILs originating from patient 1 were stimulated with irradiated autologous tumor cells in the presence of a low dose of IL-2 and of TCGF (22). After 15 days of MLTC, specific cytolytic activity against the autologous tumor cells (31% of lysis at an E:T ratio of 40/1) was detected, and TILs were cloned by the limiting dilution technique in the presence of autologous tumor cells, EBV-transformed B cells and allogenic PBLs, and with addition of IL-2 and of TCGF. A TCRα/β+ CF8+ clone, termed 3B8, was isolated. It lyses the autologous RCC cell line, but not the NK-sensitive K562 target cells. The cytotoxicity of clone 3B8 against the autologous RCC-1 cell line, with mAb W6/32, was blocked (FIG. 1A). In both the cytotoxicity (FIG. 1B) and TNF production assays, all the allogenic HLA-B7+ RCC cell lines (RCC-2, RCC-4 and RCC-5 in FIG. 1B) and none of the HLA-B7-RCC cell lines (RCC-7, RCC-6, RCC-7 and RCC-8) are recognized by 3B8. Consequently, the antigen recognized by 3B8 is presented by the HLA-B7 molecule and turns out to be commonly expressed in the RCC cell lines. The 6 class I HLA molecules were isolated from RCC-1 by RT-PCR (33), were cloned into pcDNAI and were sequenced. The nucleotide sequence of the autologous HLA-B7 cDNA made it possible to identify the allele involved as being HLA-B*0702. A transfection of this HLA allele into two HLA-B7$^-$ allogenic RCC cell lines proves sufficient to induce recognition (TNF secretion) by the CTL clone 3B8, confirming the fact that this clone has led to the identification of a shared antigen which is expressed by all RCCs.

EXAMPLE 3

Clonal Expansion in situ of a TIL Subpopulation with TCRVB-BC and TCRVB-BJ CDR3 Lengths which are Similar to the RCC-specific CTL Clone 3B8

For clone 3B8, a signal was obtained with only one of the 24 Vβ subfamily primers (TCRVB5) and only one of the 13 TCRBJ primers (TCRBJ1S2) tested. The analysis of CDR3 size distribution showed that the TCRBV5J1S2 clonotype of 3B8 is dominant in the tumor (as indicated by the TCRBV5-BC primers in FIG. 2A and by the TCRBV5-BJ12 primers for a more refined analysis in FIG. 2B), whereas such a clonotype was not found in the PBMCs (a virtually Gaussian distribution of CDR3 length with the TCRBV-BC primers, see FIG. 2A). This result strongly suggests that clone 3B8 underwent expansion specifically in the tumor site, as previously shown in several cases by cDNA sequencing (14, 34–36).

EXAMPLE 4

Identification of a cDNA Encoding the Antigen

A cDNA library originating from RNA extracted from the RCC-1 cell line was constructed in the expression vector pcDNAI. This cDNA library was divided into 400 groups of 200 recombined plasmids, and each group was cotransfected, in duplicate, into COS-7 cells along with the expression vector pcDNAI containing the cDNA encoding the autologous HLA-B*0702. The ability of the COS-7 cells to stimulate TNF production by 3B8 was tested. After 48 hours, the cotransfected COS-7 cells were incubated for 24 hours with 3B8, and measured the TNF concentration in the culture supernatants was measured via its cytotoxic effect on WEHI cells. The amounts of TNF found in the supernatants range from 8 to 11 pg/ml, except for two duplicate pairs which have higher amounts (14 and 15 pg/ml). For each group of bacteria corresponding to these candidate wells, the plasmid DNA was extracted and subcloned. A second screening was carried out by transfecting COS-7 cells with 50 groups of 50 recombined plasmids which were extracted from positive duplicates. Finally, a third screening in COS-7 cells led to the isolation of 2 identical cDNA clones (cDNA clones 2C2 and 3G7) which transfer the expression of the antigen into HLA-B7' COS-7 cells. The results obtained with these cDNA clones are represented in FIG. 3A.

The 2C2 cDNA sequence is 1250 nt long and has 100% homology over nt 763 to 2009 (the nt being numbered starting from the nonsense codon) with a recently identified cDNA which encodes a putative intestinal carboxylesterase (31). In order to identify the full length iCE cDNA corresponding to the published sequence, an RT-PCR was carried out starting from total RNA extracted from an RCC cell line, and the corresponding 1.6-kb PCR product was subcloned into the vector pcDNAI and then sequenced. The nucleotide sequence is identical to the published iCE sequence. Cotransfection experiments in COS-7 cells showed that the full length iCE cDNA is capable of conferring recognition by 3B8.

EXAMPLE 5

Identification of the Antigenic Peptide

In order to delimit the minimum nucleotide region encoding the antigenic peptide, various truncated cDNAs, corresponding to the iCE coding region, were obtained from the 2C2 cDNA clone (FIG. 4). These cDNA fragments, which had been subcloned into the expression vector pcDNAI, were transfected into COS-7 cells together with pcDNAI containing the autologous HLA-B*0702 cDNA. A minimum nucleotide coding region is located between nucleotides 763 and 1033.

In order to reduce the nucleotide sequence encoding the antigen, several truncated cDNAs were obtained by PCR amplification. These truncated cDNAS were cotransfected with the HLA-B*0702 allele into COS-7 cells. The COS-7 cells transfected with a fragment ranging from nucleotides 763 to 855 are recognized by the CTL clone 3B8, but those transfected with a fragment ranging from nucleotides 763 to 834 (FIG. 4) are not, indicating that the peptide coding region is located between nucleotides 763 and 855. After examining the corresponding amino acid sequence, all possible nonamers and decamers were synthesized, and their ability to make autologous EBV-transformed B cells sensitive to lysis by 3B8 was evaluated. None of them proved to be positive at $10^{-4}$ or $10^{-5}$ M.

Finally, an alternative ORF was found (a+1 translational open reading frame leading to a 453-nt ORF) with three ATGs in nt positions 476, 479 and 803, which encodes a nonamer (SPRWWPTCL) (SEQ ID NO: 2) in the minimum region of nt 763–855. This nonamer sequence comprises HLA-B7-anchoring residues in positions 2, 3 and 9. Semi-maximum lysis of EBV-transformed B cells was obtained with less the $10^{-6}$ M of this nonapeptide (FIG. 5).

EXAMPLE 6

Binding of the iCE Peptide to HLA-B7

HLA-A2-binding peptide antigens upregulate the expression of HLA-A2 molecules on T2 cells (37). Similarly, T2 cells transfected with HLA-B*0702 (38) were used to analyze the binding capacity and the stability of the iCE peptide (FIG. 6). At 50 mM, the binding of the iCE peptide is stable over time for at least 4 h, unlike the control, which is the HLA-A2-restricted HSP70 peptide (14).

EXAMPLE 7

Tissue Distribution of iCE mRNA

In order to determine the tissue determination of iCE messengers, a human RNA Master blot™ (Clontech, Palo Alto, USA), consisting of a nylon membrane on which poly(A)+ RNAs originating from 50 human tissues had been immobilized in individual spots, was hybridized with the $^{32}$P-labeled cDNA of clone 2C2, which was used as a probe. The iCE mRNA was detected in the liver, the kidney, the small intestine, the colon and the heart, and it was weakly expressed in the hypophysis, the adrenal gland, the prostate and the stomach. No signal was found in fetal tissues, in bone marrow, in peripheral leukocytes, in the lung and in the brain. In order to identify the mRNA species, a Northern blot was prepared with the poly(A)+ RNA originating from various RCC cell lines and untransformed renal cell lines (FIG. 7A), as well as with the total RNA extracted from various primary tumors, namely renal tumors, a melanoma, a bladder tumor, a neuroblastoma and a colon tumor (FIG. 7B). The RNA blot was hybridized with a cDNA probe corresponding to nucleotides 1033–2009 of the 2C2 sequence. As shown in FIG. 7A, two mRNA species (4.5 kb and 3.5 kb), which had been previously described by Schwer et al. (31), were detected in RCC carcinoma cell lines, as well as in untransformed renal cells. In the primary renal tumors, a single mRNA transcription product (3.5 kb) is detectable, whereas no iCE transcription product was detected in primary tumors with different histotypes (FIG. 7B). Although an additional transcription product of 2.2 kb has been indicated (31) in the small intestine and the liver, no such transcription product was detected in the various cell lines or primary tumors tested for. Thus, in RCC tumors, the iCE protein is encoded from a single mRNA species which is predominantly expressed (3.5 kb).

EXAMPLE 8

A non-AUG Cryptic Codon Initiates an Alternative Open Reading Frame

A stop codon was first of all introduced into position 807 of the full length iCE cDNA (FIG. 8A), just before the nonamer coding sequence, in order to confirm that the peptide recognized in the cytotoxicity assays is encoded by the corresponding sequence in COS-7 transfection assays. This point mutation (mutant A) abolishes CTL clone 3B8 recognition after cotransfection with HLA-B*0702 in COS cells (8B). The natural AUG translation start site was mutated at position 3, and this point mutant (mutant B) proved to still be recognized (FIG. 8), indicating that neither the natural amino acid sequence of iCE, nor a chimeric sequence resulting from a programmed translational frameshift (i.e. a sliding of the ribosome in iCE from a codon in a forward direction) and from a recoding of the downstream sequence (39, 40), encodes the recognized peptide.

Figure 8B:
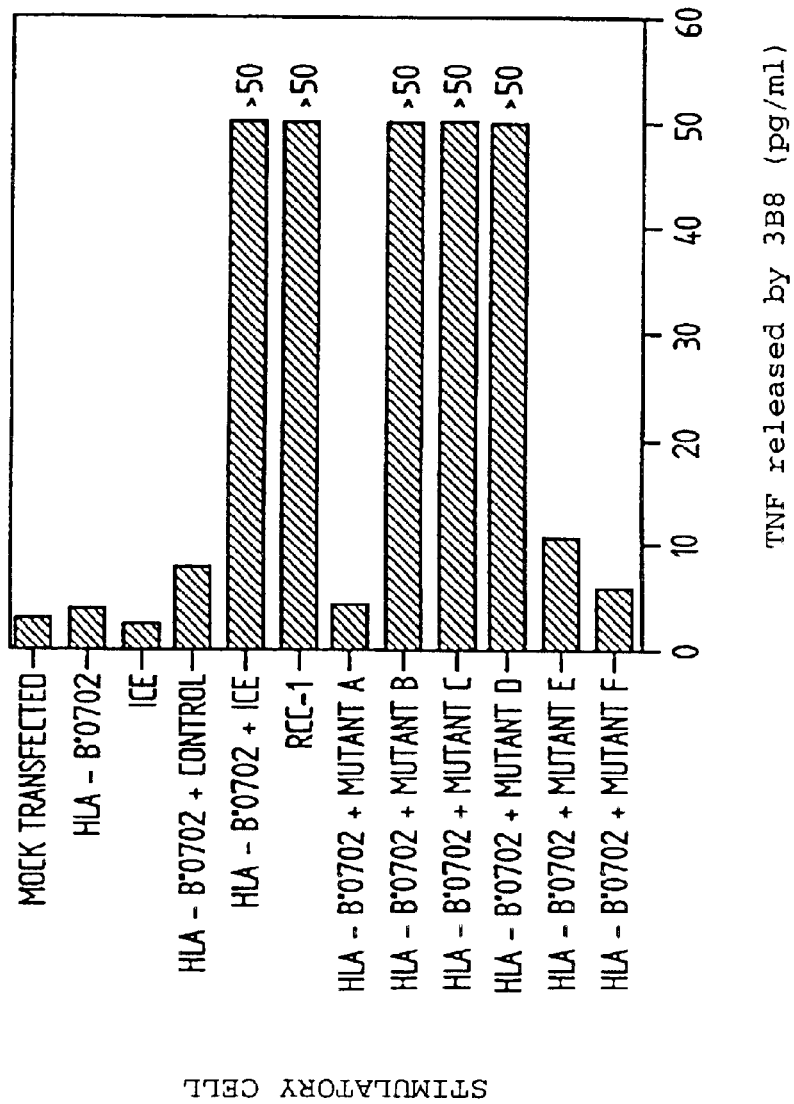

In addition to the ribosomal frameshift (41), a ribosomal scanning mechanism which initiates translation at a downstream ATG proved to lead to the production of alternative reading frames which are recognized by T cells (42). Point mutations in the full length iCE cDNA were introduced at each of the three ATG sites which were found in the +1 ORF upstream of the nonamer peptide (mutant C for positions 476 and 479, and mutant D at position 803), in order to test whether the corresponding mutated iCE pcDNAI hybrids were still capable of conferring recognition by CTL clone 3B8 in TNF-release assays, when they were cotransfected with HLA-B*0702 in COS cells. As shown in FIG. 8B, none of these mutations abolishes recognition by CTL clone 3B8. These results demonstrate that a non-AUG cryptic codon is used in the iCE cDNA as an alternative translation start site.

In order to delimit the minimum nucleotide region encoding this non-ATG cryptic codon, stop codons which should interrupt the +1 ORF were introduced at various positions upstream of the antigenic peptide (between positions 428 and 809), with point mutations at positions 466 (mutant E), 519, 666 and 786 of the full length iCE cDNA (FIG. 8A). These four mutants abolish all CTL clone 3B8 recognition after cotransfection (see in FIG. 8B the result of mutant E for position 446). A minimum nucleotide region was then located between nt 428 and 466. Possible non-ATG codons (CTG, ACG) were then sought in this short sequence, and an ACG codon at position 440 was found. Mutation of this codon into ACT (mutant F) abolishes CTL clone 3B8 recognition (FIG. 8B). Thus, the first non-AUG codon in the +1 ORF was used to initiate the translation process.

REFERENCES

1. Van der Bruggen, P., C. Traversari, P. Chomez, C. Lurquin, E. D. Plaen, B. V. d. Eynde, A. Knuth, and T. Boon. 1991. A gene encoding an antigen recognized by cytolytic T lymphocytes on a human melanoma. Science 254:1643.
2. Van den Eynde, B., and V. G. Brichard. 1995. New tumor antigens recognized by T cells. Curr. Opin. Immunol. 7:674.
3. Gaugler, B., B. V. d. Eynde, P. Van den Bruggen, P. Romero, J. J. Gaforio, E. D. Plaen, B. Lethe, F. Brasseur, and T. Boon. 1994. Human gene MAGE-3 codes for an antigen recognized on a melanoma by autologous cytolytic T lymphocytes. J. Exp. Med. 179:921.
4. Boel, P., C. Wildmann, M. L. Sensi, R. Brasseur, J. C. Renauld, P. Coulie, T. Boon, and P. Van den Bruggen. 1995. BAGE: a new gene encoding an antigen recognized on human melanomas by cytolytic T lymphocytes. Immunity 2:167.
5. Coulie, P. G., V. Brichard, A. V. Pel, T. Wölfel, J. Schneider, C. Traversari, S. Mattei, E. D. Plaen, C. Lurquin, J. P. Szikora, J. C. Renauld, and T. Boon. 1994. A new gene coding for a differentiation antigen recognized by autologous cytolytic T lymphocytes on HLA-A2 melanomas. J. Exp. Med. 180:35.
6. Kawakami, Y., S. Eliyahu, K. Sakaguchi, P. F. Robbins, L. Rivoltini, J. R. Yanelli, E. Apella, and S. A. Rosenberg. 1994. Identification of the immunodominant peptides of the MART-1 human melanoma antigen recognized by the majority of HLA-A2-restricted tumor infiltrating lymphocytes. J. Exp. Med. 180:347.
7. Brichard, V., A. V. Pel T. Wölfel, C. Wölfel, E. D. Plaen, B. Lethé, P. Coulie, and T. Boon. 1993. The tyrosinase gene codes for an antigen recognized by autologous cytolytic T lymphocytes on HLA-A2 melanomas. J. Exp. Med. 178:489.
8. Robbins, P. F., M. El-Gamil, Y. F. Li, S. L. Topalian, L. Rivoltini, K. Sakaguchi, E. Appella, Y. Kawakami, and S. A. Rosenberg. 1995. Cloning of a new gene—encoding an antigen recognized by melanoma-specific HLA-A24-restricted tumor—infiltrating lymphocytes. J. Immunol. 154:5944.
9. Wang, R. F., P. F. Robbins, Y. Kawakami, X. Q. Kang, and S. A. Rosenberg. 1995. Identification of a gene encoding a melanoma tumor antigen recognized by HLA-A31-restricted tumor-infiltrating lymphocytes. J. Exp. Med. 181:799.
10. Robbins, P. F., M. El-Gamil, Y. F. Li, Y. Kawakami, D. Loftus, E. Appella, and S. A. Rosenberg. 1996. A mutated beta-catenin gene encodes a melanoma-specific antigen recognized by tumor infiltrating lymphocytes. J. Exp. Med. 183:1185.
11. Coulie, P. G., F. Lehmann, B. Lethe, J. Herman, C. Lurquin, M. Andrawiss, and T. Boon. 1995. A mutated intron sequence codes for an antigenic peptide recognized by cytolytic T lymphocytes on a human melanoma. Proc. Natl. Acad. Sci. USA 92:7976.
12. Wölfel, T., M. Hauer, J. Schneider, M. Serrano, C. Wolfel, E. Klehmann-Hieb, E. D. Plaen, T. Hankeln, K. H. M. z. Buschenfelde, and D. Beach. 1995. A p16ink4a-insensitive CDK4 mutant targeted by cytolytic T lymphocytes in a human melanoma. Science 269:1281.
13. Brandle, D., F. Brasseur, P. Weynants, T. Boon, and B. J. V. d. Eynde. 1996. A mutated HLA-A2 molecule recognized by autologous cytotoxic T lymphocytes on a human renal cell carcinoma. J. Exp. Med. 183:2501.
14. Gaudin, C., F. Kremer, E. Angevin, V. Scott, and F. Triebel. 1999. A HSP70-2 mutation recognized by cytolytic T lymphocytes on a human renal cell carcinoma. J. Immunol. 162:1730.
15. Guilloux, Y., S. Lucas, V. G. Brichard, A. VanPel, C. Viret, E. D. Plaen, F. Brasseur, B. Lethe, F. Jotereau, and T. Boon. 1996. A peptide recognized by human cytolytic T lymphocytes on HLA-A2 melanoma is encoded by an intron sequence of the N-acetylglucosaminyltransferase V gene. J. Exp. Med. 183:1173.
16. Robbins, P. F., M. El-Gamil, Y. F. Li, E. B. Fitzgerald, Y. Kawakami, and S. A. Rosenberg. 1997. The intronic region of an incompletely spliced gp100 gene transcript encodes an epitope recognized by melanoma-reactive tumor-infiltrating lymphocytes. J. Immunol. 159:303.
17. Wang, R. F., E. Appella, Y. Kawakami, X. Kang, and S. A. Rosenberg. 1996. Identification of TRP-2 as a human tumor antigen recognized by cytotoxic T lymphocytes, J. Exp. Med. 184:2207.
18. Wang, R. F., S. L. Johnston, G. Zeng, S. L. Topalian, D. J. Schwartzentruber, and S. A. Rosenberg. 1998. A breast and melanoma-shared tumor antigen: T cell responses to antigenic peptides translated from different open reading frames. J Immunol 161:3598.
19. Nanbru, C., I. Lafon, S. Audigier, M. C. Gensac, S. Vagner, G. Huez, and A. C. Prats. 1997. Alternative translation of the proto-oncogene c-myc by an internal ribosome entry site. J. Biol. Chem. 272:32061.
20. Vagner, S., C. Touriol, B. Galy, S. Audigier, M. C. Gensac, F. Almaric, F. Bayard, H. Prats, and A. C. Prats. 1996. Translation of CUG- but not AUG-initiated forms of human fibroblast growth factor 2 is activated in transformed and stressed cells. J. Cell. Biol. 135:1391.
21. Galy, B., A. Maret, A. C. Prats, and H. Prats. 1999. Cell transformation results in the loss of the density-dependent translational regulation of the expression of fibroblast growth factor 2 isoforms. Cancer Res. 59:165.
22. Angevin, E., F. Kremer, C. Gaudin, T. Hercend, and F. Triebel. 1997. Analysis of T-cell immune response in renal cell carcinoma: polarization to type 1-like differentiation pattren, clonal T cell expansion and tumor-specific cytotoxicity. Int. J. Cancer 72:431.
23. Seed, B. 1987. An LFA-3 cDNA encodes a phospholipid-linked membrane protein homologous to its receptor CD2. Nature 329:840.
24. Traversari, C., P. Van der Bruggen, I. F. Luescher, C. Lurquin, P. Chomez, A. Van Pel, E. De Plaen, A. Amar-Costesec, and T. Boon. 1992. A nonapeptide encoded by 25. Espevik, T., and J. Nissen-Meyer. 1986. A highly sensitive cell line, WEHI 164 clone 13, for measuring cytotoxic factor/tumor necrosis factor from human monocytes. J. Immunol. Methods 95:99.
26. Genevee, C., A. Diu, J. Nierat, A. Caignard, P. Y. Dietrich, L. Ferradini, S. Roman—Roman, F. Triebel, and T. Hercend. 1992. An experimentally validated panel of subfamily-specific oligonucleotide primers (V□1-w29/V□1-w24) for the study of human T cell receptor variable V gene segment usage by polymerase chain reaction. Eur. J. Immunol 22:1261.
27. Even, J., A. Lim, I. Puisieux, L. Ferradini, P. Y. Dietrich, A. Toubert, T. Hercend, F. Triebel, C. Pannetier, and P. Kourilsky. 1995. T-cell repertoires in healthy and diseased human tissues analysed by T-cell receptor □-chain CDR3 size determination: evidence for oligoclonal expansions in tumours and inflammatory diseases. Res. Immunol. 146:65.
28. Pannetier, C., M. Cochet, S. Darche, A. Casrouge, M. Zoller, and P. Kourilsky. 1993. The sizes of the CDR3 hypervariable regions of the murine T-cell receptor □ chains vary as a function of the recombined germ-line segments. Proc. Natl. Acad. Sci. USA 90:2472.
29. Birnboim, H. C., and J. Doly. 1979. A rapid alkaline extraction procedure for screening recombinant plasmid DNA. Nucleic Acid Res 7:1513.
30. Sambrook, J., E. Fritsch, and T. Maniatis. 1989. Molecular cloning: a laboratory manual. Cold Spring Harbor Laboratory Press, Cold Spring Harbor, N.Y.
31. Schwer, H., T. Langmann, R. Daig, A. Becker, C. Aslanidis, and G. Schmitz. 1997. Molecular cloning and characterization of a novel putative carboxylesterase, present in human intestine and liver. Biochem. Biophys. Res. Comm. 233:117.
32. Mikaelian, I., and A. Sergeant. 1992. A general and fast method to generate multiple site directed mutations. Nuc. Ac. Res. 20:376.
33. Ennis, P. D., J. Zemmour, R. D. Salter, and P. Parham. 1990. Rapid cloning of HLA-A,B cDNA by using the polymerase chain reaction: Frequency and nature of errors produced in amplification. Proc. Natl. Acad. Sci.USA 87:2833.
34. Farace, F., F. Orlanducci, P. Y. Dietrich, C. Gaudin, E. Angevin, M. H. Courtier, C. Bayle, T. Hercend, and F. Triebel. 1994. T cell repertoire in patients with B-chronic lymphocytic leukemia: evidence for multiple in vivo T cell clonal expansions. J. Immunol. 153:4281.
35. Farace, F., E. Angevin, I. Poullion, C. Leboullaire, G. Ferir, D. Elias, B. Escudier, and F. Triebel. 1997. T-cell receptor CDR3 size distribution analysis to evaluate specific T-cell response to cancer vaccines. Int. J. Cancer 71:972.
36. Gaudin, C., P. Y. Dietrich, S. Robache, M. Guillard, B. Escudier, M. J. Terrier-Lacombe, A. Kumar, F. Triebel, and A. Caignard. 1995. In vivo local expansion of clonal T cell subpopulations in renal cell carcinoma. Cancer Res. 55:685.
37. Nijman, H. W., J. G. Houbiers, M. P. Vierboom, S. H. v. d. Burg, J. W. Drijfhout, J. D'Amaro, P. Kenemans, C. J. Melief, and W. M. Kast. 1993. Identification of peptide sequences that potentially trigger HLA-A2.1-restricted cytotoxic T lymphocytes. Eur. J. Immunol. 23:1215.
38. Smith, K. D., and C. T. Lutz. 1996. Peptide-dependent expression of HLA-B7 on antigen processing deficient T2 cells. J. Immunol. 156:3755.
39. Farabaugh, P. J. 1996. Programmed translational frameshifting. Annu. Rev. Genet. 30:507.
40. Matsufuji, S., T. Matsufuji, Y. Miyazaki, Y. Murakami, J. F. Atkins, R. F. Gesteland, and S. Hayashi. 1995. Autoregulatory frameshifting in decoding mammalian ornithine decarboxylase antizyme. Cell 80:51.
41. Elliott, T., H. Bodmer, and A. Townsend. 1996. Recognition of out-of-frame major histocompatibility complex class I-restricted epitopes in vivo. Eur J Immunol 26:1175.
42. Bullock, T. N. J., and L. C. Eisenlohr. 1996. Ribosomal scanning past the primary initiation codon as a mechanism for expression of CTL epitopes encoded in alternative reading frames. J. Exp. Med. 184:1319.

What is claimed is:

1. A recombinant or chemically synthesized peptide compound, comprising SEQ ID NO:1 or a fragment thereof, wherein the fragment comprises SEQ ID NO:2, and wherein the peptide causes a specific T response.

2. The peptide compound of claim 1 consisting of SEQ ID NO:2.

3. The peptide compound of claim 1, characterized in that it comprises at least one element other than natural amino acids selected from the group consisting of protective chemical groups and fatty acids covalently bonded to the peptide.

4. A composition comprising a peptide compound as claimed in claim 1 and a pharmaceutically acceptable vehicle.

5. The composition of claim 4, further comprising one or more immunological adjuvants which are cytotoxic for tumors.

6. The composition of claim 4, further comprising a pharmaceutical vehicle which is compatible with IV, subcutaneous, oral or nasal administration.

7. The composition of claim 4, further comprising a pharmaceutical vehicle selected from positively or negatively charged liposomes, nanoparticles or lipid emulsions.

* * * * *

SEQUENCE LISTING

<160> NUMBER OF SEQ ID NOS: 9

<210> SEQ ID NO 1
<211> LENGTH: 162
<212> TYPE: PRT
<213> ORGANISM: Homo sapiens

<400> SEQUENCE: 1

Thr Val Val Arg Leu Phe Leu Ala Trp Leu Pro Cys Met Met Val Pro
 1               5                  10                  15

Cys Trp Leu Pro Trp Arg Thr Trp Trp Ser Ser Ser Thr Ala
            20                  25                  30

Trp Val Ser Trp Ala Ser Ser Ala Leu Glu Thr Ser Thr Gln Pro Ala
        35                  40                  45

Thr Gly Ala Thr Trp Thr Lys Trp Leu His Tyr Ala Gly Ser Ser Arg
    50                  55                  60

```
Ile Ser Pro Thr Leu Glu Ala Thr Leu Thr Val Ser Pro Phe Leu Ala
 65                  70                  75                  80

Ser Leu Arg Val Ala Arg Val Cys Leu Arg Leu Cys Pro Pro Tyr
                 85                  90                  95

Pro Lys Asp Ser Ser Thr Glu Pro Ser Trp Arg Val Ala Trp Pro Ser
            100                 105                 110

Cys Pro Ala Ser Leu Pro Ala Gln Leu Met Ser Ser Pro Arg Trp Trp
        115                 120                 125

Pro Thr Cys Leu Pro Val Thr Lys Leu Thr Leu Arg Pro Trp Trp Ala
    130                 135                 140

Ala Cys Gly Ala Arg Val Lys Arg Arg Phe Leu Gln Leu Thr Ser Leu
145                 150                 155                 160

Ser Arg

<210> SEQ ID NO 2
<211> LENGTH: 9
<212> TYPE: PRT
<213> ORGANISM: Homo sapiens

<400> SEQUENCE: 2

Ser Pro Arg Trp Trp Pro Thr Cys Leu
  1               5

<210> SEQ ID NO 3
<211> LENGTH: 521
<212> TYPE: DNA
<213> ORGANISM: Homo sapiens

<400> SEQUENCE: 3
acggtggtgc gcttgttttt ggcatggctt ccttgtatga tggttccatg ctggctgcct      60
tggagaacgt ggtggtggtc atcatccagt accgcctggg tgtcctggc ttcttcagca     120 ctggagacaa gcacgcaacc ggcaactggg gctacctgga ccaagtggct gcactacgct     180
gggtccagca gaatatcgcc cactttggag gcaaccctga ccgtgtcacc atttttggcg     240
agtctgcggg tggcacgagt gtgtcttcgc ttgttgtgtc ccccatatcc caaggactct     300
tccacggagc catcatggag agtggcgtgg ccctcctgcc cggcctcatt gccagctcag     360
ctgatgtcat ctccacggtg gtggccaacc tgtctgcctg tgaccaagtt gactctgagg     420
ccctggtggg ctgcctgcgg ggcaagagta aagaggagat tcttgcaatt aacaagcctt     480
tcaagatgat ccccggagtg gtggatgggg tcttcctgcc c                        521

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
cccaagcttg gtgaatagca gcgtgtccgc                                       30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer
```

<400> SEQUENCE: 5
tgctctagaa gggagctaca gctctgtgtg                                   30

<210> SEQ ID NO 6
<211> LENGTH: 1680
<212> TYPE: DNA
<213> ORGANISM: Homo sapiens
<220> FEATURE:
<221> NAME/KEY: CDS
<222> LOCATION: (1)..(1677)

<400> SEQUENCE: 6

| | | |
|---|---|---|
| atg cgg ctg cac aga ctt cgt gcg cgg ctg agc gcg gtg gcc tgt ggg<br>Met Arg Leu His Arg Leu Arg Ala Arg Leu Ser Ala Val Ala Cys Gly<br>1               5                   10                  15 | 48 |
| ctt ctg ctg ctt ctt gtc cgg ggc cag ggc cag gac tca gcc agt ccc<br>Leu Leu Leu Leu Leu Val Arg Gly Gln Gly Gln Asp Ser Ala Ser Pro<br>            20                  25                  30 | 96 |
| atc cgg acc aca cac acg ggg cag gtg ctg ggg agt ctt gtc cat gtg<br>Ile Arg Thr Thr His Thr Gly Gln Val Leu Gly Ser Leu Val His Val<br>        35                  40                  45 | 144 |
| aag ggc gcc aat gcc ggg gtc caa acc ttc ctg gga att cca ttt gcc<br>Lys Gly Ala Asn Ala Gly Val Gln Thr Phe Leu Gly Ile Pro Phe Ala<br>    50                  55                  60 | 192 |
| aag cca cct cta ggt ccg ctg cga ttt gca ccc cct gag ccc cct gaa<br>Lys Pro Pro Leu Gly Pro Leu Arg Phe Ala Pro Pro Glu Pro Pro Glu<br>65                  70                  75                  80 | 240 |
| tct tgg agt ggt gtg agg gat gga acc acc cat ccg gcc atg tgt cta<br>Ser Trp Ser Gly Val Arg Asp Gly Thr Thr His Pro Ala Met Cys Leu<br>                85                  90                  95 | 288 |
| cag gac ctc acc gca gtg gag tca gag ttt ctt agc cag ttc aac atg<br>Gln Asp Leu Thr Ala Val Glu Ser Glu Phe Leu Ser Gln Phe Asn Met<br>            100                 105                 110 | 336 |
| acc ttc cct tcc gac tcc atg tct gag gac tgc ctg tac ctc agc atc<br>Thr Phe Pro Ser Asp Ser Met Ser Glu Asp Cys Leu Tyr Leu Ser Ile<br>        115                 120                 125 | 384 |
| tac acg ccg gcc cat agc cat gaa ggc tct aac ctg ccg gtg atg gtg<br>Tyr Thr Pro Ala His Ser His Glu Gly Ser Asn Leu Pro Val Met Val<br>    130                 135                 140 | 432 |
| tgg atc cac ggt ggt gcg ctt gtt ttt ggc atg gct tcc ttg tat gat<br>Trp Ile His Gly Gly Ala Leu Val Phe Gly Met Ala Ser Leu Tyr Asp<br>145                 150                 155                 160 | 480 |
| ggt tcc atg ctg gct gcc ttg gag aac gtg gtg gtg atc atc cag<br>Gly Ser Met Leu Ala Ala Leu Glu Asn Val Val Val Ile Ile Gln<br>                165                 170                 175 | 528 |
| tac cgc ctg ggt gtc ctg ggc ttc ttc agc act gga gac aag cac gca<br>Tyr Arg Leu Gly Val Leu Gly Phe Phe Ser Thr Gly Asp Lys His Ala<br>            180                 185                 190 | 576 |
| acc ggc aac tgg ggc tac ctg gac caa gtg gct gca cta cgc tgg gtc<br>Thr Gly Asn Trp Gly Tyr Leu Asp Gln Val Ala Ala Leu Arg Trp Val<br>        195                 200                 205 | 624 |
| cag cag aat atc gcc cac ttt gga ggc aac cct gac cgt gtc acc att<br>Gln Gln Asn Ile Ala His Phe Gly Gly Asn Pro Asp Arg Val Thr Ile<br>    210                 215                 220 | 672 |
| ttt ggc gag tct gcg ggt ggc acg agt gtg tct tcg ctt gtt gtg tcc<br>Phe Gly Glu Ser Ala Gly Gly Thr Ser Val Ser Ser Leu Val Val Ser<br>225                 230                 235                 240 | 720 |
| ccc ata tcc caa gga ctc ttc cac gga gcc atc atg gag agt ggc gtg<br>Pro Ile Ser Gln Gly Leu Phe His Gly Ala Ile Met Glu Ser Gly Val<br>                245                 250                 255 | 768 |

```
                                              -continued gcc ctc ctg ccc ggc ctc att gcc agc tca gct gat gtc atc tcc acg      816
Ala Leu Leu Pro Gly Leu Ile Ala Ser Ser Ala Asp Val Ile Ser Thr
        260                 265                 270 gtg gtg gcc aac ctg tct gcc tgt gac caa gtt gac tct gag gcc ctg      864
Val Val Ala Asn Leu Ser Ala Cys Asp Gln Val Asp Ser Glu Ala Leu
            275                 280                 285 gtg ggc tgc ctg cgg ggc aag agt aaa gag gag att ctt gca att aac      912
Val Gly Cys Leu Arg Gly Lys Ser Lys Glu Glu Ile Leu Ala Ile Asn
290                 295                 300 aag cct ttc aag atg atc ccc gga gtg gtg gat ggg gtc ttc ctg ccc      960
Lys Pro Phe Lys Met Ile Pro Gly Val Val Asp Gly Val Phe Leu Pro
305                 310                 315                 320 agg cac ccc cag gag ctg ctg gcc tct gcc gac ttt cag cct gtc cct     1008
Arg His Pro Gln Glu Leu Leu Ala Ser Ala Asp Phe Gln Pro Val Pro
                325                 330                 335 agc att gtt ggt gtc aac aac aat gaa ttc ggc tgg ctc atc ccc aag     1056
Ser Ile Val Gly Val Asn Asn Asn Glu Phe Gly Trp Leu Ile Pro Lys
            340                 345                 350 gtc atg agg atc tat gat acc cag aag gaa atg gac aga gag gcc tcc     1104
Val Met Arg Ile Tyr Asp Thr Gln Lys Glu Met Asp Arg Glu Ala Ser
355                 360                 365 cag gct gct ctg cag aaa atg tta acg ctg ctg atg ttg cct cct aca     1152
Gln Ala Ala Leu Gln Lys Met Leu Thr Leu Leu Met Leu Pro Pro Thr
370                 375                 380 ttt ggt gac ctg ctg agg gag gag tac att ggg gac aat ggg gat ccc     1200
Phe Gly Asp Leu Leu Arg Glu Glu Tyr Ile Gly Asp Asn Gly Asp Pro
385                 390                 395                 400 cag acc ctc caa gcg cag ttc cag gag atg atg gcg gac tcc atg ttt     1248
Gln Thr Leu Gln Ala Gln Phe Gln Glu Met Met Ala Asp Ser Met Phe
                405                 410                 415 gtg atc cct gca ctc caa gta gca cat ttt cag tgt tcc cgg gcc cct     1296
Val Ile Pro Ala Leu Gln Val Ala His Phe Gln Cys Ser Arg Ala Pro
            420                 425                 430 gtg tac ttc tac gag ttc cag cat cag ccc agc tgg ctc aag aac atc     1344
Val Tyr Phe Tyr Glu Phe Gln His Gln Pro Ser Trp Leu Lys Asn Ile
435                 440                 445 agg cca ccg cac atg aag gca gac cat ggt gat gag ctt cct ttt gtt     1392
Arg Pro Pro His Met Lys Ala Asp His Gly Asp Glu Leu Pro Phe Val
450                 455                 460 ttc aga agt ttc ttt ggg ggc aac tac att aaa ttc act gag gaa gag     1440
Phe Arg Ser Phe Phe Gly Gly Asn Tyr Ile Lys Phe Thr Glu Glu Glu
465                 470                 475                 480 gag cag cta agc agg aag atg atg aag tac tgg gcc aac ttt gcg aga     1488
Glu Gln Leu Ser Arg Lys Met Met Lys Tyr Trp Ala Asn Phe Ala Arg
                485                 490                 495 aat ggg aac ccc aat ggc gag ggt ctg cca cac tgg ccg ctg ttc gac     1536
Asn Gly Asn Pro Asn Gly Glu Gly Leu Pro His Trp Pro Leu Phe Asp
            500                 505                 510 cag gag gag caa tac ctg cag ctg aac cta cag cct gcg gtg ggc cgg     1584
Gln Glu Glu Gln Tyr Leu Gln Leu Asn Leu Gln Pro Ala Val Gly Arg
515                 520                 525 gct ctg aag gcc cac agg ctc cag ttc tgg aag aag gcg ctg ccc caa     1632
Ala Leu Lys Ala His Arg Leu Gln Phe Trp Lys Lys Ala Leu Pro Gln
530                 535                 540 aag atc cag gag ctc gag gag cct gaa gag aga cac aca gag ctg tag     1680
Lys Ile Gln Glu Leu Glu Glu Pro Glu Glu Arg His Thr Glu Leu
545                 550                 555
```

<210> SEQ ID NO 7
<211> LENGTH: 559
<212> TYPE: PRT
<213> ORGANISM: Homo sapiens

<400> SEQUENCE: 7

```
Met Arg Leu His Arg Leu Arg Ala Arg Leu Ser Ala Val Ala Cys Gly
 1               5                  10                  15

Leu Leu Leu Leu Val Arg Gly Gln Gly Gln Asp Ser Ala Ser Pro
            20                  25                  30

Ile Arg Thr Thr His Thr Gly Gln Val Leu Gly Ser Leu Val His Val
            35                  40                  45

Lys Gly Ala Asn Ala Gly Val Gln Thr Phe Leu Gly Ile Pro Phe Ala
 50                  55                  60

Lys Pro Pro Leu Gly Pro Leu Arg Phe Ala Pro Pro Glu Pro Pro Glu
 65                  70                  75                  80

Ser Trp Ser Gly Val Arg Asp Gly Thr Thr His Pro Ala Met Cys Leu
                85                  90                  95

Gln Asp Leu Thr Ala Val Glu Ser Glu Phe Leu Ser Gln Phe Asn Met
            100                 105                 110

Thr Phe Pro Ser Asp Ser Met Ser Glu Asp Cys Leu Tyr Leu Ser Ile
            115                 120                 125

Tyr Thr Pro Ala His Ser His Glu Gly Ser Asn Leu Pro Val Met Val
            130                 135                 140

Trp Ile His Gly Gly Ala Leu Val Phe Gly Met Ala Ser Leu Tyr Asp
145                 150                 155                 160

Gly Ser Met Leu Ala Ala Leu Glu Asn Val Val Val Ile Ile Gln
                165                 170                 175

Tyr Arg Leu Gly Val Leu Gly Phe Phe Ser Thr Gly Asp Lys His Ala
            180                 185                 190

Thr Gly Asn Trp Gly Tyr Leu Asp Gln Val Ala Ala Leu Arg Trp Val
            195                 200                 205

Gln Gln Asn Ile Ala His Phe Gly Gly Asn Pro Asp Arg Val Thr Ile
        210                 215                 220

Phe Gly Glu Ser Ala Gly Gly Thr Ser Val Ser Ser Leu Val Val Ser
225                 230                 235                 240

Pro Ile Ser Gln Gly Leu Phe His Gly Ala Ile Met Glu Ser Gly Val
                245                 250                 255

Ala Leu Leu Pro Gly Leu Ile Ala Ser Ser Ala Asp Val Ile Ser Thr
            260                 265                 270

Val Val Ala Asn Leu Ser Ala Cys Asp Gln Val Asp Ser Glu Ala Leu
        275                 280                 285

Val Gly Cys Leu Arg Gly Lys Ser Lys Glu Glu Ile Leu Ala Ile Asn
    290                 295                 300

Lys Pro Phe Lys Met Ile Pro Gly Val Val Asp Gly Val Phe Leu Pro
305                 310                 315                 320

Arg His Pro Gln Glu Leu Leu Ala Ser Ala Asp Phe Gln Pro Val Pro
                325                 330                 335

Ser Ile Val Gly Val Asn Asn Asn Glu Phe Gly Trp Leu Ile Pro Lys
            340                 345                 350

Val Met Arg Ile Tyr Asp Thr Gln Lys Glu Met Asp Arg Glu Ala Ser
            355                 360                 365

Gln Ala Ala Leu Gln Lys Met Leu Thr Leu Leu Met Leu Pro Pro Thr
    370                 375                 380
```

```
Phe Gly Asp Leu Leu Arg Glu Glu Tyr Ile Gly Asp Asn Gly Asp Pro
385                 390                 395                 400

Gln Thr Leu Gln Ala Gln Phe Gln Glu Met Met Ala Asp Ser Met Phe
            405                 410                 415

Val Ile Pro Ala Leu Gln Val Ala His Phe Gln Cys Ser Arg Ala Pro
            420                 425                 430

Val Tyr Phe Tyr Glu Phe Gln His Gln Pro Ser Trp Leu Lys Asn Ile
        435                 440                 445

Arg Pro Pro His Met Lys Ala Asp His Gly Asp Glu Leu Pro Phe Val
        450                 455                 460

Phe Arg Ser Phe Phe Gly Gly Asn Tyr Ile Lys Phe Thr Glu Glu Glu
465                 470                 475                 480

Glu Gln Leu Ser Arg Lys Met Met Lys Tyr Trp Ala Asn Phe Ala Arg
                485                 490                 495

Asn Gly Asn Pro Asn Gly Glu Gly Leu Pro His Trp Pro Leu Phe Asp
                500                 505                 510

Gln Glu Glu Gln Tyr Leu Gln Leu Asn Leu Gln Pro Ala Val Gly Arg
            515                 520                 525

Ala Leu Lys Ala His Arg Leu Gln Phe Trp Lys Lys Ala Leu Pro Gln
530                 535                 540

Lys Ile Gln Glu Leu Glu Glu Pro Glu Glu Arg His Thr Glu Leu
545                 550                 555

<210> SEQ ID NO 8
<211> LENGTH: 166
<212> TYPE: PRT
<213> ORGANISM: Homo sapiens

<400> SEQUENCE: 8

Trp Cys Gly Ser Thr Val Val Arg Leu Phe Leu Ala Trp Leu Pro Cys
  1               5                  10                  15

Met Met Val Pro Cys Trp Leu Pro Trp Arg Thr Trp Trp Trp Ser Ser
            20                  25                  30

Ser Ser Thr Ala Trp Val Ser Trp Ala Ser Ser Ala Leu Glu Thr Ser
        35                  40                  45

Thr Gln Pro Ala Thr Gly Ala Thr Trp Thr Lys Trp Leu His Tyr Ala
    50                  55                  60

Gly Ser Ser Arg Ile Ser Pro Thr Leu Glu Ala Thr Leu Thr Val Ser
 65                  70                  75                  80

Pro Phe Leu Ala Ser Leu Arg Val Ala Arg Val Cys Leu Arg Leu Leu
                85                  90                  95

Cys Pro Pro Tyr Pro Lys Asp Ser Ser Thr Glu Pro Ser Trp Arg Val
            100                 105                 110

Ala Trp Pro Ser Cys Pro Ala Ser Leu Pro Ala Gln Leu Met Ser Ser
        115                 120                 125

Pro Arg Trp Trp Pro Thr Cys Leu Pro Val Thr Lys Leu Thr Leu Arg
    130                 135                 140

Pro Trp Trp Ala Ala Cys Gly Ala Arg Val Lys Arg Arg Phe Leu Gln
145                 150                 155                 160

Leu Thr Ser Leu Ser Arg
                165

<210> SEQ ID NO 9
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Val Ile Ser Thr Val Val Ala Asn Leu
 1               5
```